US008940876B2

(12) United States Patent
Kim et al.

(10) Patent No.: US 8,940,876 B2
(45) Date of Patent: Jan. 27, 2015

(54) METHOD FOR PREPARING RECOMBINANT GLYCOPROTEINS WITH HIGH SIALIC ACID CONTENT

(75) Inventors: Jung Hoe Kim, Daejeon (KR); Young Dok Son, Daejeon (KR); Jin Young Hwang, Daejeon (KR); Yeon Tae Jeong, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 13/390,671

(22) PCT Filed: Feb. 1, 2011

(86) PCT No.: PCT/KR2011/000755
§ 371 (c)(1),
(2), (4) Date: Feb. 15, 2012

(87) PCT Pub. No.: WO2011/096750
PCT Pub. Date: Aug. 11, 2011

(65) Prior Publication Data
US 2012/0149874 A1    Jun. 14, 2012

(30) Foreign Application Priority Data

Feb. 8, 2010   (KR) .................. 10-2010-0011528
Feb. 1, 2011   (KR) .................. 10-2011-0010312

(51) Int. Cl.
| C07K 14/505 | (2006.01) |
| C07K 14/705 | (2006.01) |
| C07K 14/52 | (2006.01) |
| C12P 21/00 | (2006.01) |
| C12N 9/90 | (2006.01) |
| C12N 9/12 | (2006.01) |
| C12N 9/10 | (2006.01) |

(52) U.S. Cl.
CPC ............. *C07K 14/505* (2013.01); *C07K 14/524* (2013.01); *C12P 21/005* (2013.01); *C12N 9/90* (2013.01); *C07K 14/705* (2013.01); *C12Y 501/03014* (2013.01); *C12N 9/1205* (2013.01); *C12N 9/1081* (2013.01)
USPC ........... 530/395; 435/197; 435/193; 435/455; 435/254.2; 530/383; 530/398; 530/397

(58) Field of Classification Search
CPC combination set(s) only.
See application file for complete search history.

(56) References Cited

U.S. PATENT DOCUMENTS

| 6,949,372 B2 | 9/2005 | Betenbaugh et al. |
| 2002/0045207 A1 | 4/2002 | Krummen et al. |
| 2009/0298120 A1 | 12/2009 | Wong et al. |

OTHER PUBLICATIONS

Bork et al (Increasing the Sialylation of Therapeutic Glycoproteins: The Potential of the Sialic Acid Biosynthetic Pathway Bork et al, Journal of Pharmaceutical Sciences, vol. 98, 3499-3508 (2009)—Published online Feb. 6, 2009.*
Galeano et al. (Jun. 2007), "Mutation in the key enzyme of sialic acid biosynthesis causes severe glomerular proteinuria and is rescued by N-acetylmannosamine," The Journal of Clinical Investigation, vol. 117, No. 6, pp. 1585-1594.
Jay et al. (Jun. 2008), "Preclinical assessment of wt GEN gene plasmid for management of hereditary inclusion body myopathy 2(HIBM2)," Gene Regulation and Systems Biology, vol. 2, pp. 243-252.
Seppala et al. (Jun. 1999), "Mutations in the human UDP-N-acetylglucosamine 2-epimerase gene define the disease sialuria and the allosteric site of the enzyme," Am. J. Hum. Genet., vol. 64, No. 6, pp. 1563-1569.
International Search Report for PCT/KR2011/000755, mailed Oct. 20, 2011.
Angata, T. and Varki, A. (2002), "Chemical Diversity in the Sialic Acids and Related α-Keto Acids: An Evolutionary Perspective", Chem. Rev., 102, 439-469.
Ngantung F.A. et al. (2006), "RNA Interference of Sialidase Improves Glycoprotein Sialic Acid Content Consistency", Biotechnology and Bioengineering, 95(1),106-119.
Takeuchi M, et al., (1989), "Relationship between sugar chain structure and biological activity of recombinant human erythropoietin produced in Chinese hamster ovary cells", Proc. Natl Acad. Sci., vol. 86, pp. 7819-22.
Inoue N. et al. (1999), "Asn-linked sugar chain structures of recombinant human thrombopoietin produced in Chinese hamster ovary cells", Glycoconjugate Journal, 16, 707-718.
Fukuda, M. N. et al. (1989), "Survival of recombinant erythropoietin in the circulation: the role of carbohydrates", Blood 73, 84-89.
Sinclair, A. M. et al. (2005), "Glycoengineering: The Effect of Glycosylation on the Properties of Therapeutic Proteins", J. Pharm. Sci. 94, 1626-1635.

* cited by examiner

*Primary Examiner* — Kagnew H Gebreyesus
(74) *Attorney, Agent, or Firm* — Lathrop & Gage LLP

(57) ABSTRACT

The present disclosure relates to a method for preparing recombinant glycoproteins with high sialic acid content. More specifically, for UDP-GlcNAc 2-epimerase/ManNAc kinase (GNE/MNK) enzyme where point mutation was induced by substituting arginine at position 263 by leucine only or by further substituting arginine at position 266 by glutamine, epimerase activity is constantly maintained, and overexpressed cells thereof experience an increase in intracellular cytidine monophosphate (CMP)-sialic acid content, irrespective of CMP-sialic acid concentration. Particularly, since in an glycoprotein (such as, erythropoietin and thrombopoietin)-producing host cell where point mutationinduced GNE/MNK, human alpha-2,3-sialyltransferase and a CMP-sialic acid transporter gene are simultaneously overexpressed, intracellular content of CMP-sialic acid and sialic acid in glycoprotein increases in cells, overexpression in a host cell producing a sialylated recombinant glycoprotein the three genes above may be useful for preparing glycoprotein with increased sialic acid content.

4 Claims, 13 Drawing Sheets

1 : EC2-1H9
2 : EC2-1H9 supplemented with 5.0 mM ManNAc
3 : EC2-1H9-rEK-R263L 3
4 : EC2-1H9-rEK-R263L II-7
5 : EC2-1H9-rEK-R263L II-12
6 : EC2-1H9-rEK-R263L-R266Q 4
7 : EC2-1H9-rEK-R263L-R266Q 7
8 : EC2-1H9-rEK-R263L-R266Q II-1.

Fig. 8
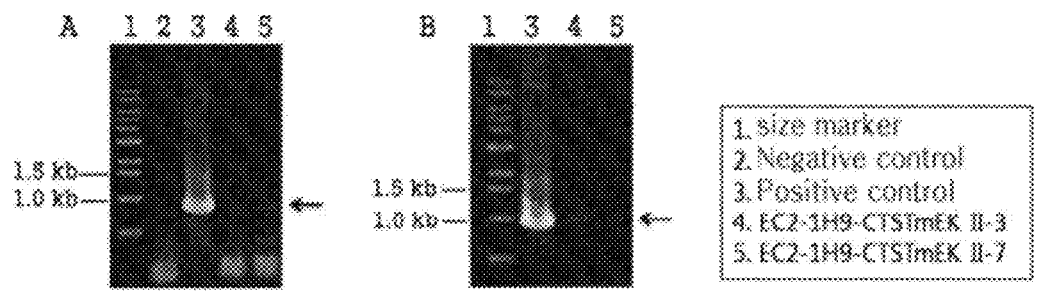
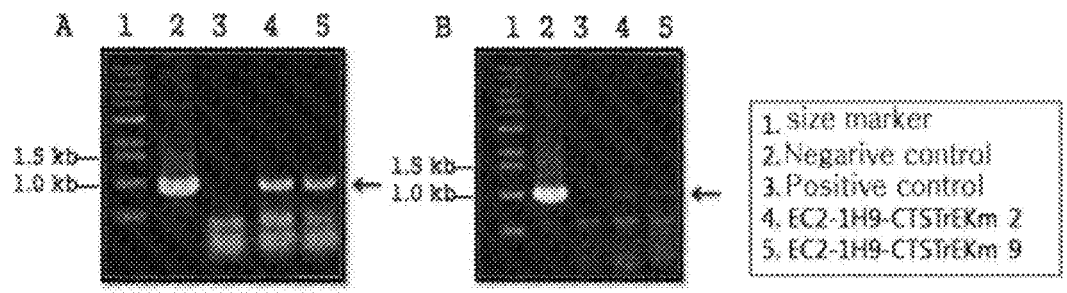

```
                         SEQUENCE LISTING

<160> NUMBER OF SEQ ID NOS: 30

<210> SEQ ID NO 1
<211> LENGTH: 722
<212> TYPE: PRT
<213> ORGANISM: Rattus norvegicus

<400> SEQUENCE: 1

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

Lys Thr Glu Pro Ala Phe Phe Glu Leu Asp Val Val Leu Gly Ser
            35                  40                  45

His Leu Ile Asp Asp Tyr Gly Asn Thr Tyr Arg Met Ile Glu Gln Asp
        50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
                100                 105                 110

Arg Phe Asp Ala Leu Ala Leu Ala Thr Ser Ala Ala Leu Met Asn Ile
            115                 120                 125

Arg Ile Leu His Ile Glu Gly Gly Glu Val Ser Gly Thr Ile Asp Asp
        130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Cys Lys Asp Tyr Ile Val Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335
```

```
Ala Asp Thr Gln Asp Lys Ile Leu Gln Ala Leu His Leu Gln Phe Gly
                340                 345                 350

Lys Gln Tyr Pro Cys Ser Lys Ile Tyr Gly Asp Gly Asn Ala Val Pro
            355                 360                 365

Arg Ile Leu Lys Phe Leu Lys Ser Ile Asp Leu Gln Glu Pro Leu Gln
        370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Ser Leu
        435                 440                 445

Ile Leu Gln Met Cys Val Glu Ala Ala Glu Ala Val Lys Leu Asn
450                 455                 460

Cys Arg Ile Leu Gly Val Gly Ile Ser Thr Gly Gly Arg Val Asn Pro
465                 470                 475                 480

Gln Glu Gly Val Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Met Ala Glu Arg Lys Phe
        515                 520                 525

Gly Gln Gly Lys Gly Gln Glu Asn Phe Val Thr Leu Ile Thr Gly Thr
530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Ser Leu Asp Gly
                565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
        595                 600                 605

Leu Leu Val Glu Gly Met Ser Val Pro Lys Asp Glu Ala Val Gly Ala
610                 615                 620

Leu His Leu Ile Gln Ala Ala Lys Leu Gly Asn Val Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
            660                 665                 670

Ser His Tyr Ile His Ile Val Arg Asp Val Ile Arg Gln Gln Ala Leu
        675                 680                 685

Ser Ser Val Gln Asp Val Asp Val Val Ser Asp Leu Val Asp Pro
690                 695                 700

Ala Leu Leu Gly Ala Ala Ser Met Val Leu Asp Tyr Thr Thr Arg Arg
705                 710                 715                 720

Ile His
```

<210> SEQ ID NO 2
<211> LENGTH: 722
<212> TYPE: PRT
<213> ORGANISM: Rattus norvegicus -continued

<400> SEQUENCE: 2

```
Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Ala Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
        115                 120                 125

Arg Ile Leu His Ile Glu Gly Gly Glu Val Ser Gly Thr Ile Asp Asp
    130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Cys Lys Asp Tyr Ile Val Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Leu Val Met Arg Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
    370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
```

```
            405                 410                 415
Thr Asn Leu Arg Val Ala Ile Val Ser Met Lys Gly Glu Ile Val Lys
                420                 425                 430

Lys Tyr Thr Gln Phe Asn Pro Lys Thr Tyr Glu Glu Arg Ile Ser Leu
            435                 440                 445

Ile Leu Gln Met Cys Val Glu Ala Ala Glu Ala Val Lys Leu Asn
        450                 455                 460

Cys Arg Ile Leu Gly Val Gly Ile Ser Thr Gly Gly Arg Val Asn Pro
465                 470                 475                 480

Gln Glu Gly Val Val Leu His Ser Thr Lys Leu Ile Gln Glu Trp Asn
                485                 490                 495

Ser Val Asp Leu Arg Thr Pro Leu Ser Asp Thr Leu His Leu Pro Val
                500                 505                 510

Trp Val Asp Asn Asp Gly Asn Cys Ala Ala Met Ala Glu Arg Lys Phe
            515                 520                 525

Gly Gln Gly Lys Gly Gln Glu Asn Phe Val Thr Leu Ile Thr Gly Thr
        530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
                580                 585                 590

Gly Met Ala Leu Gln Arg Glu Ala Lys Lys Leu His Asp Glu Asp Leu
            595                 600                 605

Leu Leu Val Glu Gly Met Ser Val Pro Lys Asp Glu Ala Val Gly Ala
610                 615                 620

Leu His Leu Ile Gln Ala Ala Lys Leu Gly Asn Val Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
            660                 665                 670

Ser His Tyr Ile His Ile Val Arg Asp Val Ile Arg Gln Gln Ala Leu
        675                 680                 685

Ser Ser Val Gln Asp Val Asp Val Val Ser Asp Leu Val Asp Pro
690                 695                 700

Ala Leu Leu Gly Ala Ala Ser Met Val Leu Asp Tyr Thr Thr Arg Arg
705                 710                 715                 720

Ile His

<210> SEQ ID NO 3
<211> LENGTH: 722
<212> TYPE: PRT
<213> ORGANISM: Rattus norvegicus

<400> SEQUENCE: 3

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

Lys Thr Glu Pro Ala Phe Phe Glu Leu Asp Val Val Leu Gly Ser
            35                  40                  45

His Leu Ile Asp Asp Tyr Gly Asn Thr Tyr Arg Met Ile Glu Gln Asp
```

```
                50                  55                  60
Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
            115                 120                 125

Arg Ile Leu His Ile Glu Gly Gly Glu Val Ser Gly Thr Ile Asp Asp
        130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Cys Lys Asp Tyr Ile Val Ala Leu Gln His Pro Val Thr Thr
210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Leu Val Met Gln Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
        290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
    370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Ser Leu
        435                 440                 445

Ile Leu Gln Met Cys Val Glu Ala Ala Ala Glu Ala Val Lys Leu Asn
    450                 455                 460

Cys Arg Ile Leu Gly Val Gly Ile Ser Thr Gly Gly Arg Val Asn Pro
465                 470                 475                 480
```

```
Gln Glu Gly Val Val Leu His Ser Thr Lys Leu Ile Gln Glu Trp Asn
            485                 490                 495

Ser Val Asp Leu Arg Thr Pro Leu Ser Asp Thr Leu His Leu Pro Val
        500                 505                 510

Trp Val Asp Asn Asp Gly Asn Cys Ala Ala Met Ala Glu Arg Lys Phe
        515                 520                 525

Gly Gln Gly Lys Gly Gln Glu Asn Phe Val Thr Leu Ile Thr Gly Thr
        530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
            565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
        595                 600                 605

Leu Leu Val Glu Gly Met Ser Val Pro Lys Asp Glu Ala Val Gly Ala
        610                 615                 620

Leu His Leu Ile Gln Ala Ala Lys Leu Gly Asn Val Lys Ala Gln Ser
625                 630                 635                 640

Ile Leu Arg Thr Ala Gly Thr Ala Leu Gly Leu Gly Val Val Asn Ile
            645                 650                 655

Leu His Thr Met Asn Pro Ser Leu Val Ile Leu Ser Gly Val Leu Ala
            660                 665                 670

Ser His Tyr Ile His Ile Val Arg Asp Val Ile Arg Gln Gln Ala Leu
            675                 680                 685

Ser Ser Val Gln Asp Val Asp Val Val Ser Asp Leu Val Asp Pro
        690                 695                 700

Ala Leu Leu Gly Ala Ala Ser Met Val Leu Asp Tyr Thr Thr Arg Arg
705                 710                 715                 720

Ile His

<210> SEQ ID NO 4
<211> LENGTH: 375
<212> TYPE: PRT
<213> ORGANISM: Homo sapiens

<400> SEQUENCE: 4

Met Gly Leu Leu Val Phe Val Arg Asn Leu Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Glu Asp Ser Asn Ser Val Val Leu Ser Phe Asp Ser
        35                  40                  45

Ala Gly Gln Thr Leu Gly Ser Glu Tyr Asp Arg Leu Gly Phe Leu Leu
    50                  55                  60

Asn Leu Asp Ser Lys Leu Pro Ala Glu Leu Ala Thr Lys Tyr Ala Asn
65                  70                  75                  80

Phe Ser Glu Gly Ala Cys Lys Pro Gly Tyr Ala Ser Ala Leu Met Thr
            85                  90                  95

Ala Ile Phe Pro Arg Phe Ser Lys Pro Ala Pro Met Phe Leu Asp Asp
            100                 105                 110

Ser Phe Arg Lys Trp Ala Arg Ile Arg Glu Phe Val Pro Pro Phe Gly
        115                 120                 125
```

```
Ile Lys Gly Gln Asp Asn Leu Ile Lys Ala Ile Leu Ser Val Thr Lys
        130                 135                 140

Glu Tyr Arg Leu Thr Pro Ala Leu Asp Ser Leu Arg Cys Arg Arg Cys
145                 150                 155                 160

Ile Ile Val Gly Asn Gly Gly Val Leu Ala Asn Lys Ser Leu Gly Ser
                165                 170                 175

Arg Ile Asp Asp Tyr Asp Ile Val Val Arg Leu Asn Ser Ala Pro Val
            180                 185                 190

Lys Gly Phe Glu Lys Asp Val Gly Ser Lys Thr Thr Leu Arg Ile Thr
        195                 200                 205

Tyr Pro Glu Gly Ala Met Gln Arg Pro Glu Gln Tyr Glu Arg Asp Ser
    210                 215                 220

Leu Phe Val Leu Ala Gly Phe Lys Trp Gln Asp Phe Lys Trp Leu Lys
225                 230                 235                 240

Tyr Ile Val Tyr Lys Glu Arg Val Ser Ala Ser Asp Gly Phe Trp Lys
                245                 250                 255

Ser Val Ala Thr Arg Val Pro Lys Glu Pro Pro Glu Ile Arg Ile Leu
            260                 265                 270

Asn Pro Tyr Phe Ile Gln Glu Ala Ala Phe Thr Leu Ile Gly Leu Pro
        275                 280                 285

Phe Asn Asn Gly Leu Met Gly Arg Gly Asn Ile Pro Thr Leu Gly Ser
290                 295                 300

Val Ala Val Thr Met Ala Leu His Gly Cys Asp Glu Val Ala Val Ala
305                 310                 315                 320

Gly Phe Gly Tyr Asp Met Ser Thr Pro Asn Ala Pro Leu His Tyr Tyr
                325                 330                 335

Glu Thr Val Arg Met Ala Ala Ile Lys Glu Ser Trp Thr His Asn Ile
            340                 345                 350

Gln Arg Glu Lys Glu Phe Leu Arg Lys Leu Val Lys Ala Arg Val Ile
        355                 360                 365

Thr Asp Leu Ser Ser Gly Ile
        370                 375

<210> SEQ ID NO 5
<211> LENGTH: 336
<212> TYPE: PRT
<213> ORGANISM: Cricetulus griseus

<400> SEQUENCE: 5

Met Ala Gln Ala Arg Glu Asn Val Ser Leu Phe Phe Lys Leu Tyr Cys
1               5                   10                  15

Leu Ala Val Met Thr Leu Val Ala Ala Tyr Thr Val Ala Leu Arg
            20                  25                  30

Tyr Thr Arg Thr Thr Ala Lys Glu Leu Tyr Phe Ser Thr Thr Ala Val
        35                  40                  45

Cys Val Thr Glu Val Ile Lys Leu Leu Ile Ser Val Gly Leu Leu Ala
    50                  55                  60

Lys Glu Thr Gly Ser Leu Gly Arg Phe Lys Ala Ser Leu Ser Glu Asn
65                  70                  75                  80

Val Leu Gly Ser Pro Lys Glu Leu Met Lys Leu Ser Val Pro Ser Leu
                85                  90                  95

Val Tyr Ala Val Gln Asn Asn Met Ala Phe Leu Ala Leu Ser Asn Leu
            100                 105                 110

Asp Ala Ala Val Tyr Gln Val Thr Tyr Gln Leu Lys Ile Pro Cys Thr
```

```
            115                 120                 125
Ala Leu Cys Thr Val Leu Met Leu Asn Arg Thr Leu Ser Lys Leu Gln
130                 135                 140

Trp Val Ser Val Phe Met Leu Cys Gly Gly Val Ile Leu Val Gln Trp
145                 150                 155                 160

Lys Pro Ala Gln Ala Thr Lys Val Val Glu Gln Ser Pro Leu Leu
            165                 170                 175

Gly Phe Gly Ala Ile Ala Ile Ala Val Leu Cys Ser Gly Phe Ala Gly
            180                 185                 190

Val Tyr Phe Glu Lys Val Leu Lys Ser Ser Asp Thr Ser Leu Trp Val
            195                 200                 205

Arg Asn Ile Gln Met Tyr Leu Ser Gly Ile Val Val Thr Leu Val Gly
210                 215                 220

Thr Tyr Leu Ser Asp Gly Ala Glu Ile Lys Glu Lys Gly Phe Phe Tyr
225                 230                 235                 240

Gly Tyr Thr Tyr Tyr Val Trp Phe Val Ile Phe Leu Ala Ser Val Gly
            245                 250                 255

Gly Leu Tyr Thr Ser Val Val Val Lys Tyr Thr Asp Asn Ile Met Lys
            260                 265                 270

Gly Phe Ser Ala Ala Ala Ala Ile Val Leu Ser Thr Ile Ala Ser Val
            275                 280                 285

Met Leu Phe Gly Leu Gln Ile Thr Leu Ser Phe Ala Met Gly Ala Leu
            290                 295                 300

Leu Val Cys Ile Ser Ile Tyr Leu Tyr Gly Leu Pro Arg Gln Asp Thr
305                 310                 315                 320

Thr Cys Ile Gln Gln Glu Ala Thr Ser Lys Glu Arg Val Ile Gly Val
            325                 330                 335

<210> SEQ ID NO 6
<211> LENGTH: 24
<212> TYPE: DNA
<213> ORGANISM: Artificial Sequence
<220> FEATURE:
<223> OTHER INFORMATION: GNE/MNK-wild type forward primer

<400> SEQUENCE: 6
atggagaaga acgggaataa ccgg                                           24

<210> SEQ ID NO 7
<211> LENGTH: 25
<212> TYPE: DNA
<213> ORGANISM: Artificial Sequence
<220> FEATURE:
<223> OTHER INFORMATION: GNE/MNK-wild type reverse primer

<400> SEQUENCE: 7
ctagtggatc ctgcgggtcg tgtag                                          25

<210> SEQ ID NO 8
<211> LENGTH: 25
<212> TYPE: DNA
<213> ORGANISM: Artificial Sequence
<220> FEATURE:
<223> OTHER INFORMATION: Rat GNE/MNK-R263L mutated enzyme forward primer

<400> SEQUENCE: 8
ggagatggtt ctagtgatgc ggaag                                          25

<210> SEQ ID NO 9
```

```
<211> LENGTH: 25
<212> TYPE: DNA
<213> ORGANISM: Artificial Sequence
<220> FEATURE:
<223> OTHER INFORMATION: Rat GNE/MNK-R263L mutated enzyme reverse primer

<400> SEQUENCE: 9
cctctaccaa gatcactacg ccttc                                         25

<210> SEQ ID NO 10
<211> LENGTH: 25
<212> TYPE: DNA
<213> ORGANISM: Artificial Sequence
<220> FEATURE:
<223> OTHER INFORMATION: Rat GNE/MNK-R263L-R266Q mutated enzyme forward
      primer

<400> SEQUENCE: 10
ggagatggtt ctagtgatgc agaag                                         25

<210> SEQ ID NO 11
<211> LENGTH: 25
<212> TYPE: DNA
<213> ORGANISM: Artificial Sequence
<220> FEATURE:
<223> OTHER INFORMATION: Rat GNE/MNK-R263L-R266Q mutated enzyme reverse
      primer

<400> SEQUENCE: 11
cctctaccaa gatcactacg tcttc                                         25

<210> SEQ ID NO 12
<211> LENGTH: 34
<212> TYPE: DNA
<213> ORGANISM: Artificial Sequence
<220> FEATURE:
<223> OTHER INFORMATION: Rat GNE/MNK mutated enzyme forward primer

<400> SEQUENCE: 12
aattcatatg atggagaaga acgggaataa ccgg                               34

<210> SEQ ID NO 13
<211> LENGTH: 28
<212> TYPE: DNA
<213> ORGANISM: Artificial Sequence
<220> FEATURE:
<223> OTHER INFORMATION: Rat GNE/MNK mutated enzyme reverse primer

<400> SEQUENCE: 13
aatctcgagg tggatcctgc gggtcgtc                                      28

<210> SEQ ID NO 14
<211> LENGTH: 14
<212> TYPE: DNA
<213> ORGANISM: Artificial Sequence
<220> FEATURE:
<223> OTHER INFORMATION: Human alpha-2,3-sialyltransferase forward
      primer

<400> SEQUENCE: 14
atgggactct tggt                                                     14

<210> SEQ ID NO 15
<211> LENGTH: 18
<212> TYPE: DNA
<213> ORGANISM: Artificial Sequence
<220> FEATURE:
```

```
<223> OTHER INFORMATION: Human alpha-2,3-sialyltransferase reverse
      primer

<400> SEQUENCE: 15
tcagatgcca ctgcttag                                                 18

<210> SEQ ID NO 16
<211> LENGTH: 24
<212> TYPE: DNA
<213> ORGANISM: Artificial Sequence
<220> FEATURE:
<223> OTHER INFORMATION: Cricetulus griseus CMP-sialic acid transporter
      forward primer

<400> SEQUENCE: 16
cagctagcgc caccatggct cagg                                          24

<210> SEQ ID NO 17
<211> LENGTH: 26
<212> TYPE: DNA
<213> ORGANISM: Artificial Sequence
<220> FEATURE:
<223> OTHER INFORMATION: Cricetulus griseus CMP-sialic acid transporter
      reverse primer

<400> SEQUENCE: 17
tccgaattct cacacaccaa tgactc                                        26

<210> SEQ ID NO 18
<211> LENGTH: 21
<212> TYPE: DNA
<213> ORGANISM: Artificial Sequence
<220> FEATURE:
<223> OTHER INFORMATION: forward primer for RT-PCR

<400> SEQUENCE: 18
gaccaccgac attaagcatt c                                             21

<210> SEQ ID NO 19
<211> LENGTH: 21
<212> TYPE: DNA
<213> ORGANISM: Artificial Sequence
<220> FEATURE:
<223> OTHER INFORMATION: reverse primer for RT-PCR

<400> SEQUENCE: 19
gcgtcacaaa gttctcctgt c                                             21

<210> SEQ ID NO 20
<211> LENGTH: 20
<212> TYPE: DNA
<213> ORGANISM: Artificial Sequence
<220> FEATURE:
<223> OTHER INFORMATION: Human alpha-2,3-sialyltransferase forward
      primer

<400> SEQUENCE: 20
ggaggactcc aattcagtgg                                               20

<210> SEQ ID NO 21
<211> LENGTH: 21
<212> TYPE: DNA
<213> ORGANISM: Artificial Sequence
<220> FEATURE:
<223> OTHER INFORMATION: Human alpha-2,3-sialyltransferase reverse
      primer
```

<400> SEQUENCE: 21
tagccaaatc ctgcgactgc c                                            21

<210> SEQ ID NO 22
<211> LENGTH: 24
<212> TYPE: DNA
<213> ORGANISM: Artificial Sequence
<220> FEATURE:
<223> OTHER INFORMATION: Rat GNE/MNK mutated enzyme forward primer

<400> SEQUENCE: 22
gtgaccaccg acattaagca ttcc                                         24

<210> SEQ ID NO 23
<211> LENGTH: 24
<212> TYPE: DNA
<213> ORGANISM: Artificial Sequence
<220> FEATURE:
<223> OTHER INFORMATION: Rat GNE/MNK mutated enzyme reverse primer

<400> SEQUENCE: 23
gagcgtcaca aagttctcct gtcc                                         24

<210> SEQ ID NO 24
<211> LENGTH: 19
<212> TYPE: DNA
<213> ORGANISM: Artificial Sequence
<220> FEATURE:
<223> OTHER INFORMATION: Cricetulus griseus CMP-sialic acid transporter
      forward primer

<400> SEQUENCE: 24
gataagtgtt ggactttta                                               19

<210> SEQ ID NO 25
<211> LENGTH: 18
<212> TYPE: DNA
<213> ORGANISM: Artificial Sequence
<220> FEATURE:
<223> OTHER INFORMATION: Cricetulus griseus CMP-sialic acid transporter
      reverse primer

<400> SEQUENCE: 25
tcagttgata ggtaacct                                                18

<210> SEQ ID NO 26
<211> LENGTH: 33
<212> TYPE: DNA
<213> ORGANISM: Artificial Sequence
<220> FEATURE:
<223> OTHER INFORMATION: primer for induction of R263L

<400> SEQUENCE: 26
gcaaggagat ggttctagtg atgcggaaga agg                               33

<210> SEQ ID NO 27
<211> LENGTH: 33
<212> TYPE: DNA
<213> ORGANISM: Artificial Sequence
<220> FEATURE:
<223> OTHER INFORMATION: primer for induction of R266Q

<400> SEQUENCE: 27
gcaaggagat ggttcgagtg atgcagaaga agg                               33

```
<210> SEQ ID NO 28
<211> LENGTH: 33
<212> TYPE: DNA
<213> ORGANISM: Artificial Sequence
<220> FEATURE:
<223> OTHER INFORMATION: primer for induction of R266W

<400> SEQUENCE: 28
gcaaggagat ggttcgagtg atgtggaaga agg                                  33

<210> SEQ ID NO 29
<211> LENGTH: 33
<212> TYPE: DNA
<213> ORGANISM: Artificial Sequence
<220> FEATURE:
<223> OTHER INFORMATION: primer for induction of R263L-R266W

<400> SEQUENCE: 29
gcaaggagat ggttctagtg atgtggaaga agg                                  33

<210> SEQ ID NO 30
<211> LENGTH: 33
<212> TYPE: DNA
<213> ORGANISM: Artificial Sequence
<220> FEATURE:
<223> OTHER INFORMATION: primer for induction of R263L-R266Q

<400> SEQUENCE: 30
gcaaggagat ggttctagtg atgcagaaga agg                                  33
```

METHOD FOR PREPARING RECOMBINANT GLYCOPROTEINS WITH HIGH SIALIC ACID CONTENT

CROSS-REFERENCE TO RELATED APPLICATIONS

This application is a U.S. National Stage Application under 35 U.S.C. §371 of International Application No. PCT/KR2011/000755, filed Feb. 1, 2011, which claims the benefit of Korean Application No. 10-2010-0011528, filed Feb. 8, 2010, and Korean Application No. 10-2011-0010312, filed Feb. 1, 2011. All of these applications are hereby incorporated by reference in their entireties.

BACKGROUND OF THE INVENTION

1. Field of the Invention

The present disclosure relates to a method for preparing recombinant glycoproteins with high sialic acid content.

2. Description of the Related Art

Sialic acid (Sia, NeuAc, NeuGc) is a generic term for acyl derivatives of neuraminic acid (Neu). In 1936, sialic acid was first isolated by Blix from mucine of bovine salivary gland and is an acidic sugar which is composed of 9 carbons and has a COOH group. According to differences in substitution group, 50 types of sialic acids have been reported (Angata, T. and Varki, A. *Chem. Rev* 102, 439-469, 2002), which are known to be specifically distributed in species and tissues. In higher animals, sialic acid is linked to Gal, GlcNAc, GalNAc and sialic acid of glycoprotein, glycolipid, and oligosaccharide glycans by reaction of a specific sialyltransferase, respectively, through alpha-glycosidic bonding.

Since sialic acid of glycoconjugate glycan is located at the very end of a glycan structure present on a surface of a cell membrane, it has been expected to be directly involved in contact between the cell and extracellular environment, and it has been known for awhile that the lifespan of blood cells or glycoprotein in body fluid is shortened by removal of sialic acid. For example, when sialic acid on red blood cell membrane is removed (asialylation), galactose is exposed on a cell surface and binds to a receptor lectin, which specifically binds to galactose on a Kupffer cell surface. Thereby, galactose is removed from a circulatory system by a receptor-mediated endocytosis, and asialoglycoprotein, from which sialic acid is removed, is also bound by lectin on a hepatocyte surface and is removed from a circulatory system in a similar pathway to the red blood cell. Furthermore, for alpha-antitrypsin, cholinesterase, chorionic gonadotropin, CTLA4Ig, Factor VIII, gamma-glutamyltransferase, granulocyte colony-stimulating Factor (G-CSF) and luteinizing hormone (LH), which are sialylated glycoproteins, sialic acid-bound glycoprotein is reported to experience a significant increase in half life thereof, compared to sialic acid unbound glycoprotein (Ngantung F A. et al., 2006, *Biotechnol. Bioeng* 95(1), 106-119).

In particular, among sialylated glycoproteins, erythropoietin is a glycoprotein hormone which induces red blood cell generation, and a recombinant erythropoietin is being used as a therapeutic agent for anemia. Wild-type erythropoietin includes three N-glycans and one O-glycan. Since a maximum of four sialic acids may bind to one N-glycan and two sialic acids may bind to one O-glycan, potentially, 14 sialic acids in total may bind to one molecule of erythropoietin. Glycan-bound sialic acid blocks binding of asialoglycoprotein receptor present in the liver so as to prevent decomposition of erythropoietin in the liver.

Thrombopoietin (TPO) is a hormone similar to EPO produced mainly by the liver and the kidney that regulates the production of platelets in the bone marrow. TPO consists of 332 amino acids, has molecular weight approximately of 80~100 kDa, and has six N-glycans and 24 O-glycans. The first 155 amino acids are very similar to EPO, and as in the case of the glycoprotein like EPO, the sialic acid content of glycan significantly influences in vivo stability of the protein. The above was confirmed by the observance of noticeable drop of in vivo activity of TPO from which all sialic acid was removed by sialidase (Takeuchi M, et al., 1989, *Poc Natl Acad Sci*, 7819-22). Like the EPO, the structure of the glycan has the tetra-antennary, tetra-sialylation and core-fucosylation forms, and in the case of recombinant human TPO, various glycan structures have the di-antennary or heterogenous forms (Inous N, et al., 1999, *Glycoconjugate Journal*, 16, 707-718).

Accordingly, the greater the increase in sialic acid content of glycoprotein, the greater the half life of glycoprotein in a body becomes. (Fukuda, M. N. et al., 1989, Blood 73, 84-89; Sinclair, A. M. et al, 2005, J. Pharm. Sci. 94, 1626-1635) Therefore, an increase in sialic acid content is needed for quality and bioequivalence of therapeutic glycoprotein.

Accordingly, the present inventors investigated a method for increasing internal activity by increasing sialic acid content of sialylated glycoprotein such as erythropoietin and thrombopoietin. As a result, the inventors completed the present invention by identifying a significant increase in sialic acid content of erythropoietin and thrombopoietin compared to a wild type when point mutationinduced UDP-GlcNAc 2-epimerase/ManNAc kinase(GNE/MNK), CMP-sialic acid transporter (CMP-SAT) and alpha-2,3-sialyltransferase are simultaneously overexpressed in a cell producing human erythropoietin or thrombopoietin.

SUMMARY OF THE INVENTION

One object of the present invention is to provide a method for preparing recombinant glycoproteins with high sialic acid content.

In order to achieve the objects, the present invention provides a method for preparing glycoproteins with increased content of sialic acid, comprising:

1) preparing an expression vector comprising a gene encoding UDP-GlcNAc 2-epimerase/ManNAc kinase(GNE/MNK) having an amino acid sequence where an amino acid at position 263 or 266 is substituted in an amino acid sequence represented by SEQ ID NO: 1, a gene encoding alpha-2,3-sialyltransferase having an amino acid sequence represented by SEQ ID NO: 4, and a gene encoding cytidine monophosphate(CMP)-sialic acid transporter having an amino acid sequence represented by SEQ ID NO: 5;

2) transfecting the expression vector in Step 1) in a host cell producing a sialylated glycoprotein to prepare a transfectant; and 3) incubating the transfectant in Step 2) to purify a recombinant glycoprotein from the transfectant.

The present invention also provides a glycoprotein with increased sialic acid content which is prepared by the method.

Furthermore, the present invention provides a method for preparing a cell with increased intracellular content of CMP-sialic acid including:

1) preparing an expression vector comprising a gene encoding GNE/MNK having an amino acid sequence where an amino acid at position 263 or 266 is substituted in an amino acid sequence represented by SEQ ID NO: 1, a gene encoding alpha-2,3-sialyltransferase having an amino acid sequence represented by SEQ ID NO: 4, and a gene encoding CMP-sialic acid transporter having an amino acid sequence represented by SEQ ID NO: 5; and 2) transfecting the expression vector in Step 1) in a host cell to preparing a transfectant.

The present invention also provides a method for preparing a cell with increased intracellular content of CMP-sialic acid including:

1) preparing an expression vector comprising a gene encoding GNE/MNK having an amino acid sequence where an amino acid at position 263 or 266 is substituted in an amino acid sequence represented by SEQ ID NO: 1; and 2) transfecting the expression vector in Step 1) in a host cell to prepare a transfectant.

The present invention also provides a cell with increased intracellular content of CMP-sialic acid which is prepared by the method.

ADVANTAGEOUS EFFECT

In an glycoprotein producing host cell, point mutation induced GNE/MNK by substituting arginine at position 263 by leucine only, or by further substituting position 266 by glutamine or tryptophan, human alpha-2,3-sialyltransferase and CMP-sialic acid transporter gene are simultaneously overexpressed. Therefore, since intracellular CMP-sialic acid content and sialic acid in erythropoietin and thrombopoietin increases in the host cell, overexpression in the host cell producing a sialylated recombinant glycoprotein of the three genes above may be useful for preparing glycoprotein with increased sialic acid content compared to a wild type.

BRIEF DESCRIPTION OF THE DRAWINGS

The above and other objects, features and other advantages of the present invention will be more clearly understood from the following detailed description taken in conjunction with the accompanying drawings, in which:

FIG. 8 is a diagram illustrating expression of alpha-2,3-sialyltransferase (A) and point mutated GNE/MNK genes (B) transfected in Chinese hamster ovary cells;

DESCRIPTION OF THE PREFERRED EMBODIMENTS

Figure 1:
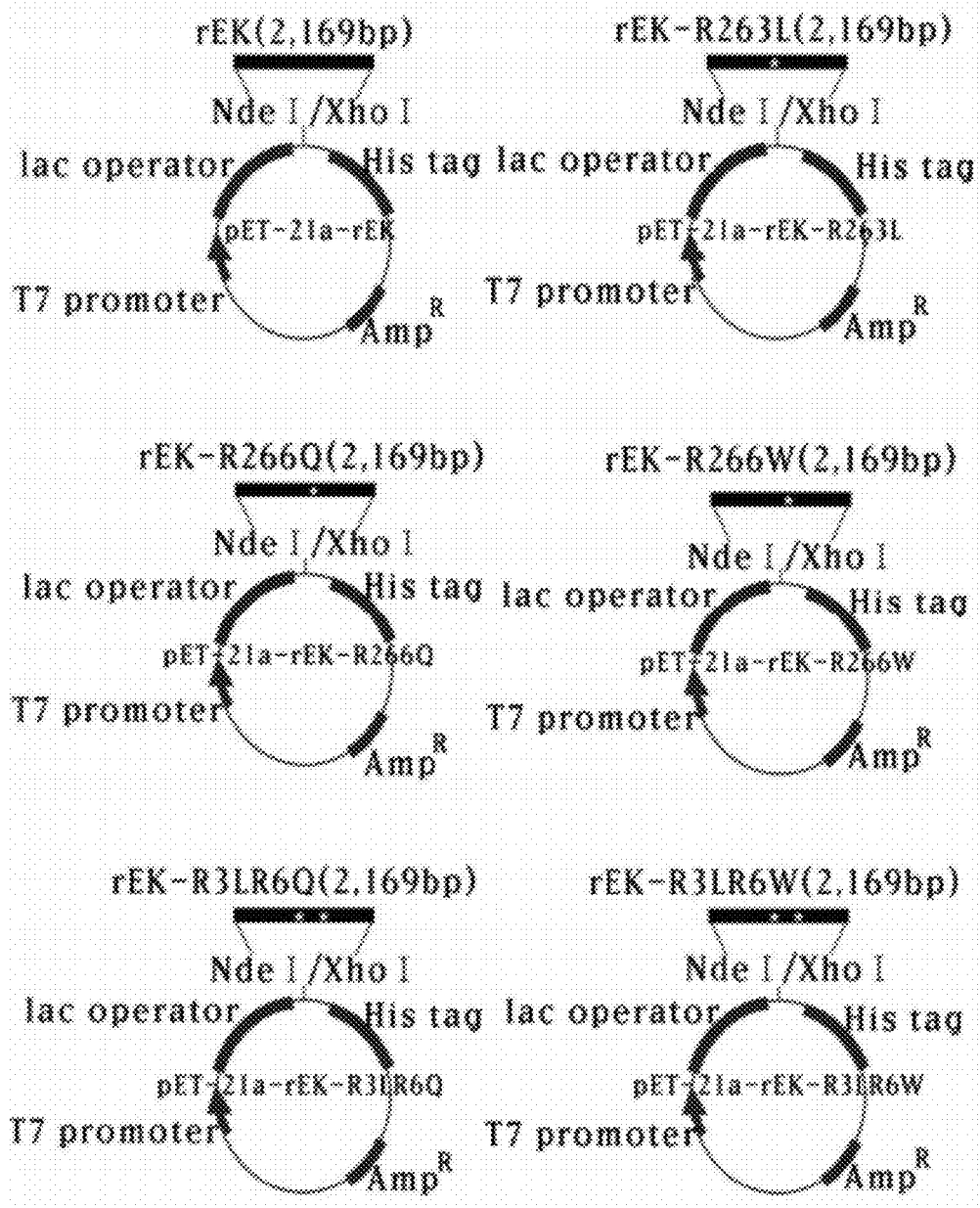
FIG. 1 is a diagram illustrating expression vector which is prepared for overexpression in microbes of mutation-induced UDP-GlcNAc 2-epimerase/ManNAc kinase (GEN/MNK) enzyme.

Hereinafter, the present invention will be described in detail.

The present invention provides a method for preparing glycoproteins with increased sialic acid content.

The method above is preferred to include, but is not limited to:

1) preparing an expression vector comprising a gene encoding UDP-GlcNAc 2-epimerase/ManNAc kinase(GNE/MNK) having an amino acid sequence where an amino acid at position 263 or 266 is substituted in an amino acid sequence represented by SEQ ID NO: 1, a gene encoding alpha-2,3-sialyltransferase having an amino acid sequence represented by SEQ ID NO: 4, and a gene encoding cytidine monophosphate(CMP)-sialic acid transporter having an amino acid sequence represented by SEQ ID NO: 5;

2) transfecting the expression vector in Step 1) in a host cell producing a sialylated glycoprotein to prepare a transfectant; and 3) incubating the transfectant in Step 2) to purify a recombinant glycoprotein from the transfectant.

The glycoprotein is preferred to be one selected from the group consisting of erythropoietin, thrombopoietin, alpha-antitrypsin, cholinesterase, chorionic gonadotropin, CTLA4Ig, Factor VIII, gamma-glutamyltransferase, granulocyte colony-stimulating Factor (G-CSF) and luteinizing hormone (LH), and erythropoietin or thrombopoietin is more preferred to be, but is not limited thereto.

In the method above, in GNE/MNK in Step 1), arginine at position 263 is preferred, but is not limited to be substituted by leucine. In the GNE/MNK, arginine at position 266 is preferred, but is not limited to be substituted by glutamine or tryptophan. In the GNE/MNK, arginine at position 263 is more preferred to be substituted by leucine and arginine at position 266 is preferred to be substituted by glutamine or tryptophan, but is not limited thereto.

In the method above, the host cell in Step 2) is preferred to be one selected from the group consisting of yeast cells, mammalian cells and insect cells, but is not limited thereto.

The mammalian cell is preferred to be one selected from the group consisting of Chinese hamster ovary cells (CHO), HT-1080, human lymphoblastoid, SP2/0 (mouse myeloma), NS0 (mouse myeloma), baby hamster kidney (BHK), human embryonic kidney cells (HEK), PERC.6 (human retinal cells), and CHO is more preferred to be, but is not limited thereto.

In the GNE/MNK having an amino acid sequence where an amino acid at position 263 or 266 is substituted, epimerase activity is preferred to be, but is not limited to be maintained irrespective of a concentration of CMP-silaic acid.

Conventionally, from the results of genetic analysis of patients suffering from hereditary metabolic pathway disease such as sialuria, point mutations (R263L, and R266Q or R266W) in genes of UDP-GlcNAc 2-epimerase/ManNAc kinase(GNE/MNK) were reported to occur from arginine amino acid at position 263 to leucine, or from arginine amino acid at position 266 to glutamine or tryptophan, which is an allosteric site of epimerase. And as CMP-sialic acid accumulates in normal-state cells, feedback inhibition thereby of epimerase enzyme disappears due to the point mutation, and sialic acid is identified to be overly synthesized and accumulated more than needed (Seppala, R. et al., 1999, *Am. J. Hum. Genet.* 64, 1563-1569). However, since there has been no study to increase sialic acid content of glycoprotein such as erythropoietin and thrombopoietin by using the feedback inhibition of epimerase enzyme, the present inventors intended to study a method for increasing sialic acid content of glycoprotein where sialic acid binds by using point mutation of GNE/MNK gene.

The present inventors intended to identify effects on epimerase activity of the enzyme by point mutation of UDP-GlcNAc 2-epimerase/ManNAc kinase (GNE/MNK) which is involved in synthesis metabolic pathway of sialic acid. Thus, the present inventors induced point mutation by substituting arginine at position 263 of wild-type GNE/MNK genes by leucine, by substituting arginine at position 266 of GNE/MNK gene by glutamine or tryptophan, or both (See FIG. 1), and included it into an expression vector to overexpress it in *Escherichia coli*. Epimerase activity was measured after overexpressed GNE/MNK enzyme was purified. As a result, for each of types of GNE/MNK where point mutation was induced, epimerase activity was shown to be maintained irrespective of increase in CMP-sialic acid concentration which is different from the wild-type GNE/MNK (See FIG. 2). Accordingly, it was found that cells expressing point-mutated GNE/MNK enzyme may synthesize and accumulate more CMP-sialic acids, compared to normal-state cells.

The present inventors, so as to identify a change in CMP-sialic acid content by overexpression of point-mutated GNE/MNK, prepared an expression vector of the point-mutated GNE/MNK (R263L or R263L-R266Q) (See FIG. 5), and transfected and overexpressed the expression vector in Chinese hamster ovary cells, which are host cells producing a recombinant erythropoietin. As a result, overexpression of point-mutated GNE/MNK gene in the host cell was identified through polymerase chain reaction (PCR) (See FIG. 6), and intracellular CMP-sialic acid content, which is used as a substrate during sialylation to a glycan end, was shown to increase compared to wild-type host cells (See FIG. 7).

The present inventors intended to study a change in sialic acid content of glycoproteins by overexpression of alpha-2,3-sialyltransferase, which is an enzyme linking sialic acid to a galactose residue of N-linked glycan, a CMP-sialic acid transporter and the point mutated GNE/MNK. Thus, the present inventors prepared an expression vector of the alpha-2,3-sialyltransferase, the CMP-sialic acid transporter and the point mutated GNE/MNK (See FIGS. 3, 4, and 5), and transfected and overexpressed the expression vector in Chinese hamster ovary cells, which are host cells producing a recombinant erythropoietin or thrombopoietin. As a result, overexpression of the three genes was all identified through PCR (See FIGS. 8 and 9), and intracellular CMP-sialic acid content was shown to increase (See FIG. 10). So as to identify isoform according to the total amount of molecular charge of erythropoietin purified from the cells, isoelectric focusing (IEF) analysis was performed in cell line where the three types of genes were introduced the whole isoforms moved into a negative electrode due to an increase in sialic acid content (See FIG. 11). Furthermore, sialic acid content of produced a recombinant erythropoietin and thrombopoietin showed a significant increase compared to wild-type cells (See FIG. 12). Additionally, the present inventors, so as to analyze more precisely the binding form of sialic acid in N-linked glycan of erythropoietin, indentified, as a result of sialylation profiling analysis of N-linked glycan through anion exchange HPLC, that a ratio of neutral-sialylated glycan and mono-sialylated glycan decreased significantly and a ratio of tetra-sialylated glycan largely increased in cell line where the three types of genes were introduced (FIG. 13). Accordingly, it has been found that by introducing alpha-2,3-sialyltransferase, CMP-sialic acid transporter and the point mutated GNE/MNK into a recombinant erythropoietin or thrombopoietin producing cell, intracellular CMP-sialic acid content increased and thereby sialic acid content of erythropoietin and thrombopoietin increased.

Therefore, alpha-2,3-sialyltransferase, CMP-sialic acid transporter and the point mutated GNE/MNK are used for preparing a glycoprotein with increased sialic acid content by overexpressing alpha-2,3-sialyltransferase, CMP-sialic acid transporter and the point mutated GNE/MNK in host cells producing a sialylated recombinant glycoprotein.

Furthermore, the present invention provides a glycoprotein with increased sialic acid content which is prepared by the method.

The glycoprotein with increased sialic acid content is preferred to be one selected from the group consisting of erythropoietin, thrombopoietin, alpha-antitrypsin, cholinesterase, chorionic gonadotropin, CTLA4Ig, Factor VIII, gamma-glutamyltransferase, granulocyte colony-stimulating Factor (G-CSF) and luteinizing hormone (LH), and erythropoietin or thrombopoietin is more preferred to be, but is not limited thereto.

The glycoprotein with increased sialic acid content is preferred, but is not limited to have a mole ratio for sialic acid/glycoprotein of 7.

GNE/MNK where point mutation was induced by substituting arginine at position 263 by leucine, or by substituting arginine at position 263 by leucine and arginine at position 266 by glutamine or tryptophan, human alpha-2,3-sialyltransferase and CMP-sialic acid transporter were simultaneously overexpressed in erythropoietin or thrombopoietin producing host cells. Since intracellular CMP-sialic acid and sialic acid content of erythropoietin and thrombopoietin increase in the erythropoietin or thrombopoietin producing host cells, a sialylated glycoprotein which is prepared by overexpression of the three genes may be used as glycoprotein with increased sialic acid content in a useful way.

Furthermore, the present invention provides a method for preparing cells with increased intracellular CMP-sialic acid content.

The method includes, but is not limited to:

1) preparing an expression vector comprising a gene encoding GNE/MNK having an amino acid sequence where an amino acid at position 263 or 266 is substituted in an amino acid sequence represented by SEQ ID NO: 1, a gene encoding alpha-2,3-sialyltransferase having an amino acid sequence represented by SEQ ID NO: 4, and a gene encoding a CMP-sialic acid transporter having an amino acid sequence represented by SEQ ID NO: 5; and 2) transfecting the expression vector in Step 1) in a host cell to prepare a transfectant.

The method further includes, but is not limited to:

1) preparing an expression vector including a gene encoding GNE/MNK having an amino acid sequence where an amino acid at position 263 or 266 is substituted in an amino acid sequence represented by SEQ ID NO: 1; and 2) transfecting the expression vector in Step 1) in a host cell to prepare a transfectant.

In the method above, 1) arginine at position 263 is preferred, but is not limited to be substituted by leucine. In the GNE/MNK arginine at position 266 is preferred, but is not limited to be substituted by glutamine or tryptophan. In the GNE/MNK arginine at position 263 is preferred to be substituted by leucine and arginine at position 266 is preferred to be substituted by glutamine or tryptophan, but is not limited thereto.

In the method above, the host cell in Step 2) is preferred to be one selected from the group consisting of yeast cells, mammalian cells and insect cells, but is not limited thereto.

The mammalian cell is preferred to be one selected from the group consisting of Chinese hamster ovary cells (CHO), HT-1080, human lymphoblastoid, SP2/0 (mouse myeloma), NS0 (mouse myeloma), baby hamster kidney (BHK), human embryonic kidney cells (HEK), PERC.6 (human retinal cells), and CHO is more preferred to be, but is not limited thereto.

The CMP-sialic acid is an active form of sialic acid and should be maintained in cells at a high level so as to increase sialic acid content of glycoproteins.

After expression vector of alpha-2,3-sialyltransferase, a CMP-sialic acid transporter and the point mutated GNE/MNK was transfected in Chinese hamster ovary cells which are host cells producing a recombinant erythropoietin or thrombopoietin, intracellular CMP-sialic acid content increased significantly compared to a wild type. After expression vector of the point mutated GNE/MNK was transfected in erythropoietin producing Chinese hamster ovary cells, intracellular CMP-sialic acid content increased significantly compared to wild-type host cells. In natural type GNE/MNK, it is known that sialic acid synthesis is eventually prevented since activity of the natural type UDP-GlcNAc 2-epimerase is prevented by feedback inhibition mechanism when concentration of CMP-sialic acid which is an intracellular precursor of sialic acid increases. Like above, intracellular CMP-sialic acid is sufficiently maintained since, by substituting specific amino acid sequence of GNE/MNK, activity in synthetic pathway of sialic acid is maintained and feedback inhibition mechanism by CMP-sialic acid makes no effect.

Therefore, point mutated GNE/MNK, alpha-2,3-sialyltransferase, and a CMP-sialic acid transporter may be used for preparing cells with increased intracellular CMP-sialic acid content in a useful way by overexpressing point mutated GNE/MNK, alpha-2,3-sialyltransferase, and the CMP-sialic acid transporter in host cells producing a sialylated recombinant glycoprotein, or by overexpressing point mutated GNE/MNK.

Furthermore, the present invention provides a cell with increased CMP-sialic acid content which is prepared by the method.

After expression vector of GNE/MNK where point mutation was induced by substituting arginine at position 263 by leucine, or by substituting arginine at position 263 by leucine and arginine at position 266 by glutamine or tryptophan, alpha-2,3-sialyltransferase and a CMP-sialic acid transporter were transfected in Chinese hamster ovary cells which are host cells producing a recombinant erythropoietin or thrombopoietin, intracellular CMP-sialic acid content increased significantly compared to a wild type. After expression vector of the point mutated GNE/MNK was transfected in erythropoietin producing Chinese hamster ovary cells, intracellular CMP-sialic acid content increased significantly compared to wild-type host cells. Like above, intracellular CMP-sialic acid is sufficiently maintained by substituting specific amino acid sequence of GNE/MNK.

Therefore, cells which are prepared by overexpressing point mutated GNE/MNK, alpha-2,3-sialyltransferase and CMP-sialic acid transporter in host cells producing a sialylated recombinant glycoprotein, or by overexpressing point mutated GNE/MNK may be used as cells with increased intracellular CMP-sialic acid content in a useful way.

Hereinafter, the present invention will be described in more detail with reference to the following examples and experimental examples.

However, the following examples and experimental examples are provided for illustrative purposes only, and the scope of the present invention should not be limited thereto in any manner.

EXAMPLE 1

Induction of Point Mutation for UDP-GlcNAc 2-Epimerase/ManNAc Kinase (GNE/MNK) Gene <1-1> Substitution of an Amino Acid at Position 263 or 266 of GNE/MNK Gene Wild-type GNE/MNK genes (SEQ ID NO: 1) were amplified through PCR by using a forward primer (5'-ATGGAGAAGAACGGGAATAACCGG-3': SEQ ID NO: 6) and a reverse primer (5'-CTAGTGGATCCTGCGGGTCGTGTAG-3': SEQ ID NO: 7) from liver tissue (obtained from Korea Advanced Institute of Science and Technology) of Rattus norvegicus, and then, a forward primer (5'-GGAGATGGTTCTAGTGATGCGAAG-3': SEQ ID NO: 8) and a reverse primer (5'-CCTCTACCAAGATCACTACGCCTTC-3':SEQ ID NO: 9) for point mutation were used to substitute arginine at position 263 by leucine (SEQ ID NO: 2) and substitute arginine at position 266 by glutamine or tryptophan through primers for induction of point mutation shown in Table 1 and QuickChange Site-Directed Mutagenesis kit (Stratagene).

<1-2> Substitution of an Amino Acid at Position 263 or 266 of GNE/MNK Gene

According to a method for Example <1-1> described above, wild-type GNE/MNK genes (SEQ ID NO: 1) were amplified through PCR by using a forward primer (5'-ATGGAGAAGAACGGGAATAACCGG-3': SEQ ID NO: 6) and a reverse primer (5'-CTAGTGGATCCTGCGGGTCGTGTAG-3': SEQ ID NO: 7), and then, another a forward primer (5'-GGAGATGGTCTAGTGATGCAGAAG-3': SEQ ID NO: 10) and a reverse primer (5'-CCTCTACCAAGATCACTACGTCTTC-3':SEQ ID NO: 11) for point mutation were used to substitute arginine at position 263 by leucine and substitute arginine at position 266 by glutamine (SEQ ID NO: 3) or tryptophan through primers for induction of point mutation shown in Table 1.

TABLE 1

A primer sequence for induction of Sialuria-like point mutation

| mutation | primer sequence |
|---|---|
| R263L | 5'-GCAAGGAGATGGTTCTAGTGATGCGGAAGAAGG-3' (SEQ ID NO: 26) |
| R266Q | 5'-GCAAGGAGATGGTTCGAGTGATGCAGAAGAAGG-3' (SEQ ID NO: 27) |
| R266W | 5'-GCAAGGAGATGGTTCGAGTGATGTGGAAGAAGG-3' (SEQ ID NO: 28) |
| R263L-R266W | 5'-GCAAGGAGATGGTTCTAGTGATGTGGAAGAAGG-3' (SEQ ID NO: 29) |
| R263L-R266Q | 5'-GCAAGGAGATGGTTCTAGTGATGCAGAAGAAGG-3' (SEQ ID NO: 30) |

<1-3> Preparation of Expression Vector in Microbes of Point Mutation-Induced GNE/MNK A forward primer (5'-AATCATATGAIGGAGAA-GAACGGGAATAACCGG-3': SEQ ID NO: 12) and a reverse primer (5'-AATCTCGAGGTGGATCCT-GCGGGTCGTC-3': SEQ ID NO: 13) where to 5'NdeI, and to 3' XhoI restriction enzyme site were added, were used. And thereby NdeI or XhoI site was formed through PCR at a terminal end of mutation-induced GNE/MNK genes, which were prepared in the Examples <1-1> and <1-2>, and wild type GNE/MNK genes. By linking mutation induced GNE/MNK gene or wild type GEN/MNK gene to NdeI/XhoI site of a pET-21a, which is a vector for protein overexpression and histidine tag in microbes, expression vectors pET-21-rEK (wildtype), pET-21-rEK-R263L (gene where arginine at position 263 were substituted by leucine), pET-21-rEK-R266Q (gene where arginine at position 266 were substituted by glutamine), pET-21-rEK-R266W (gene where arginine at position 266 were substituted by tryptophan), pET-21-rEK-R3LR6Q (gene where arginine at position 263 were substituted by leucine, and arginine at position 266 were substituted by glutamine) and pET-21-rEK-R3LR6W (gene where arginine at position 263 were substituted by leucine, and arginine at position 266 were substituted by tryptophan) were prepared as shown in FIG. 1.

<1-4> Activity Measurement of Mutation Induced GNE/MNK

A vector including wild type or mutation-induced GNE/MNK genes prepared in the Example <1-3> was introduced into BL21 Escherichia coli for protein overexpression. 0.3 mM of IPTG was injected and incubated at 20 at 200 rpm for six hours, and thereby GNE/MNK was overexpressed. The overexpressed cells were harvested through centrifugation and were lysed by using a sonic cell disruptor. After a centrifugation, a supernatant of lysed cells was incubated with Ni-NTA agarose (Qiagen) at room temperature for 1 hour. Next, Rat GNE/MNK was purified by being eluted though elution buffer (pH 8.0, mM $Na_2HPO_4$, 0.1 mM MEDTA, 300 mM NaCl and 100 mM imidazole). In purified rat GNE/MNK, epimerase activity was measured. A mixture of 45 mM $Na_2HPO_4$ (pH 7.5), 1 mM UDP-GlcNAc and eluate was reacted at 37 for 30 minutes, and the reaction was ceased by boiling. The concentration of produced N-acetyl mannosamine was measured by using Morgan-Elson method. After centrifugation, a reaction supernatant was mixed with 0.8 M borate buffer and reacted therewith at 100 for 3 minutes. And then, it was mixed with DMAB solution (1% (w/v) 4-dimethylamino benzaldehyde in acetic acid with 1.25% 10 M HCl) and was incubated at 37 for 30 minutes. Absorbance of a final mixture was measured at 578 nm by spectrometry. So as to identify activity control of epimerase by CMP-sialic acid, various concentrations of CMP-sialic acid were processed and reacted, changes in activity of CMP-sialic acid according to concentration changes, assuming an initial activity as 100.

Figure 2:
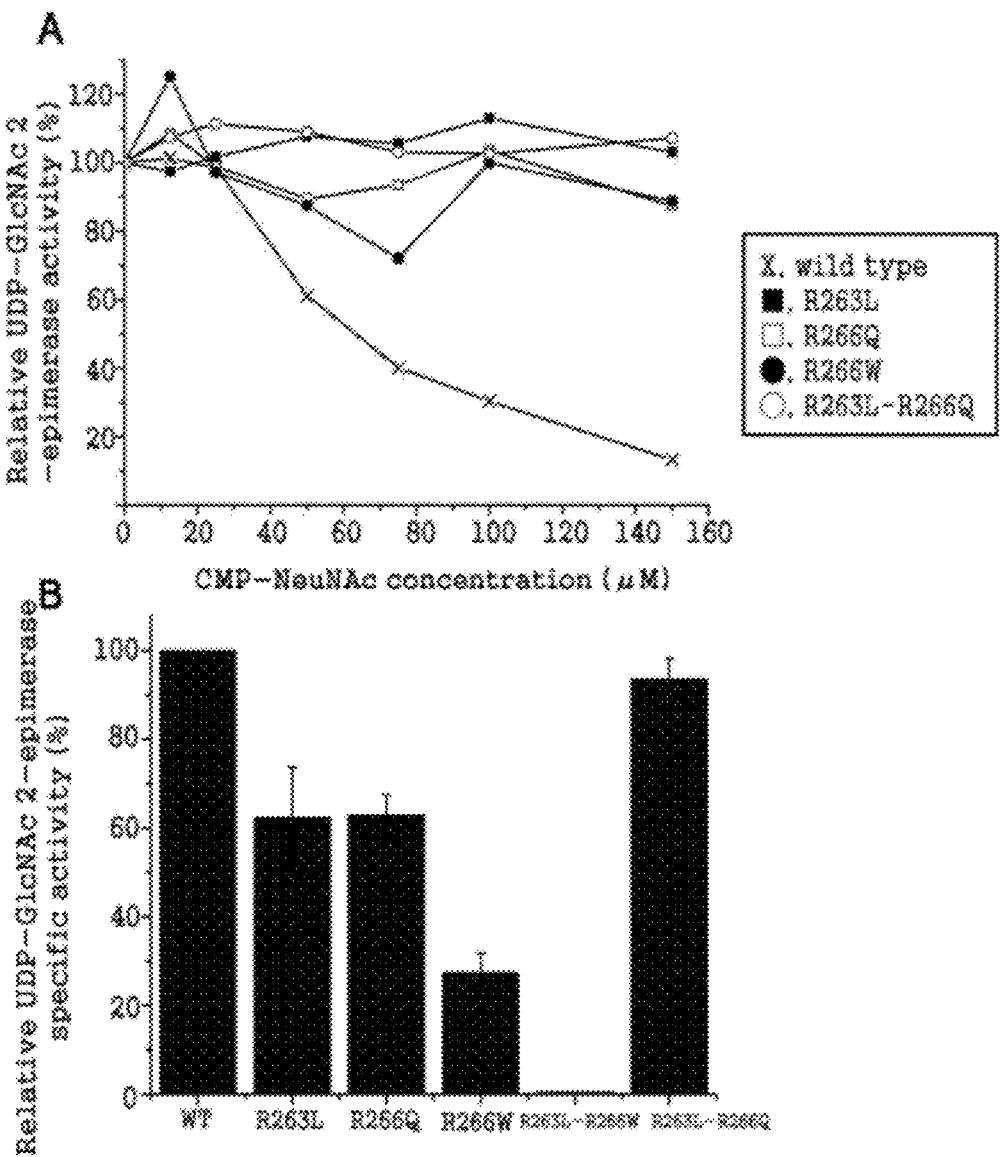
FIG. 2 is a graph illustrating epimerase activity of GNE/MNK according to CMP-sialic acid concentration (A) and relative specific activity of epimerase according to each point mutation induction (B)

As a result, as described in FIG. 2, for point mutation induced rat GNE/MNK, epimerase activity was shown to be maintained although a concentration of CMP-sialic acid increased, which is different from a wild type. Thereby, relative activity of epimerase according to each point mutation was identified (FIG. 2).

EXAMPLE 2

Preparation of Expression Vector

<2-1> Preparation of Expression Vector for Alpha-2,3-Sialyltransferase

Figure 3:
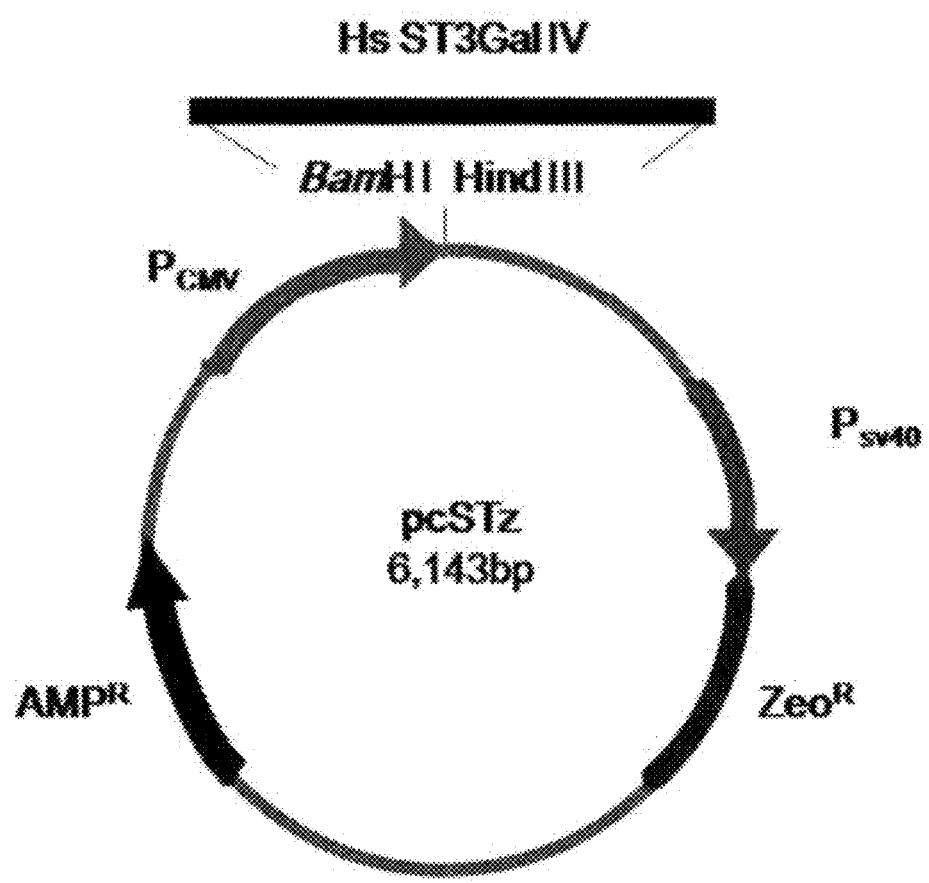
FIG. 3 is a diagram illustrating expression vector which is prepared for overexpression of alpha-2,3-sialyltransferase in Chinese hamster ovary cells.

Human alpha-2,3-sialyltransferase was amplified through polymerase chain reaction (PCR) from human fibroblast cell line (HF cell line), and a forward primer (5'-ATGGGACTCT-TGGT-3': SEQ ID NO: 14) and a reverse primer (5'-TCA-GATGCCACTGCTTAG-3': SEQ ID NO: 15) where BamHI was added to 5' and Hind was added to 3' were used. So as to introduce the amplified genes into Chinese hamster ovary cells as a host cell, as shown in FIG. 3, it was ligated to a BamHI/Hind site of an expression vector pcDNA3.1/Zeo(+) to prepare an expression vector pcSTz (FIG. 3).

Figure 4:
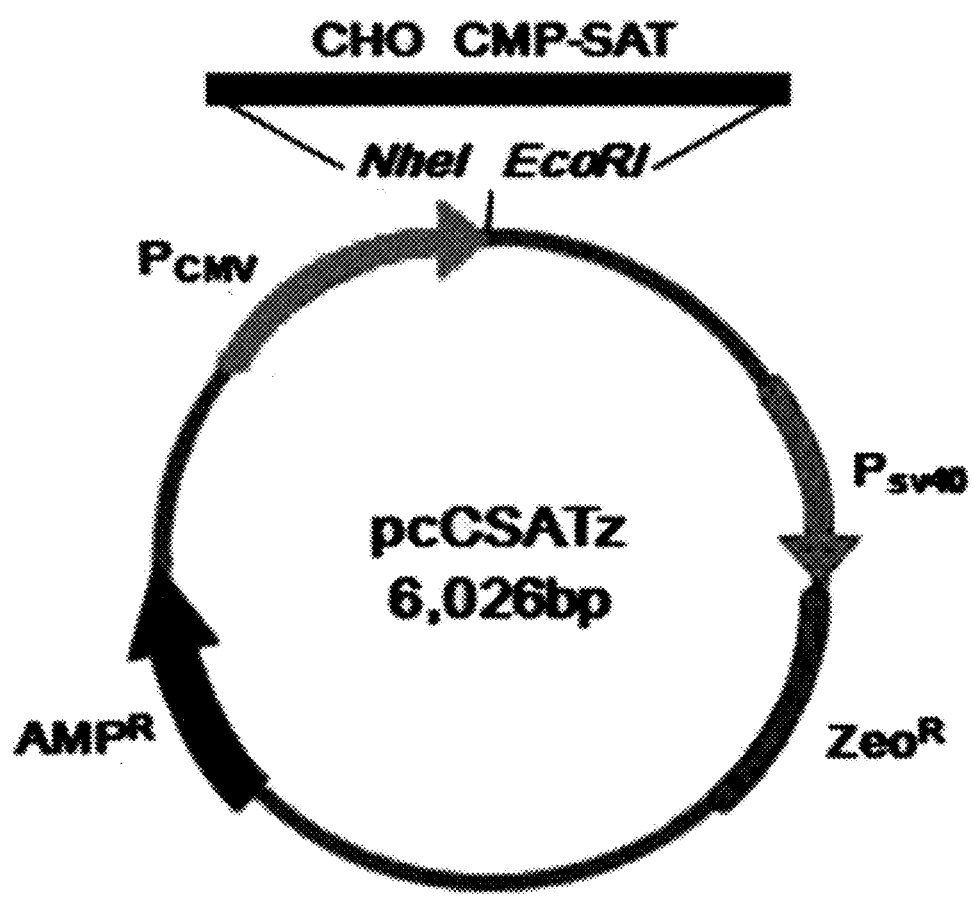
FIG. 4 is a diagram illustrating expression vector which is prepared for overexpression of CMP-sialic acid transporter in Chinese hamster ovary cells.

<2-2> Preparation of Expression Vector for Cytidine Monophosphate (CMP)-Sialic Acid Transporter cytidine monophosphate(CMP)-sialic acid transporter was amplified through PCR from Chinese hamster ovary cells (EC2-1H9: obtained from Korea Research Institute of Bioscience and Biotechnology), and a forward primer (5'-CAGCTAGCGCCACCATGGCTCAGG-3': SEQ ID NO: 16) and a reverse primer (5'-TCCGAATTCTCACACAC-CAATGACTC-3': SEQ ID NO: 17) where NheI was added to 5' and EcoRI was added to 3' were used. Thereby, NheI and EcoRI enzyme sites were added to both terminal ends of the genes. As shown in FIG. 4, the amplified gene was ligated to NheI/EcoRI site of pcDNA3.1/Zeo(+) to prepare an expression vector pcCSATz (FIG. 4).

<2-3> Preparation of Expression Vector for Point Mutation-Induced GNE/MNK

Figure 5:
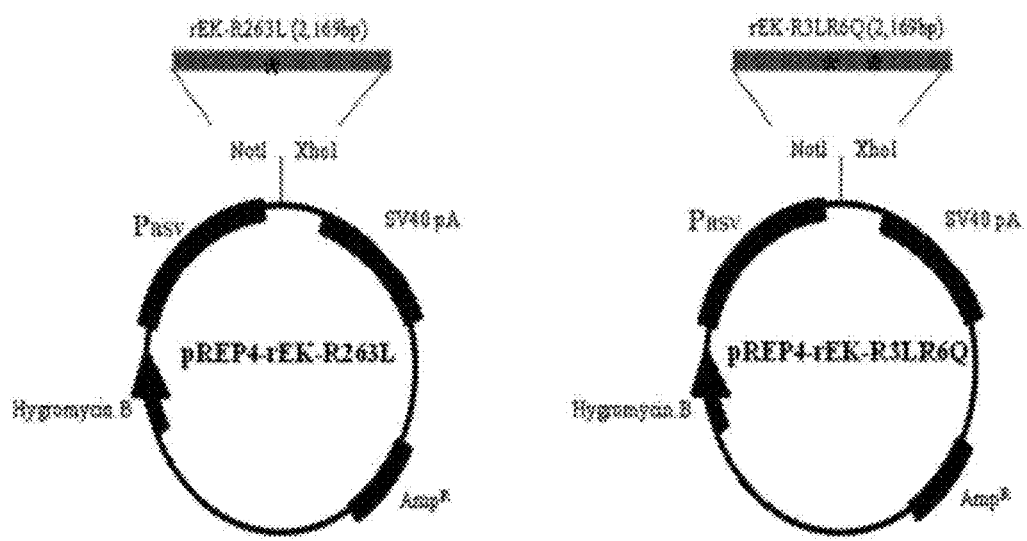
FIG. 5 is a diagram illustrating expression vector which is prepared for overexpression of point mutation-induced GNE/MNK genes in Chinese hamster ovary cells.

By using a primer where NotI restriction enzyme site was added to 5' and XhoI restriction enzyme site was added to 3', NotI or XhoI restriction enzyme site was added to both terminal ends of point mutation-induced GNE/MNK gene through PCR. As shown in FIG. 5, the amplified, point mutation-induced GNE/MNK gene was ligated to NotI/XhoI site of pREP4/Hig.B(+) expression vector to prepare expression vectors pREP4-rEK-R263L and pREP-rEK-R263L-R266Q (pREP-rEK-R3LR6Q) (FIG. 5).

EXAMPLE 3

Identification of a Change in Sialic Acid Content by Overexpression of Point Mutation-Induced GNE/MNK Gene <3-1> Introduction of Point Mutation-Induced GNE/MNK Gene Expression Vector into Chinese Hamster Ovary Cells By using Lipofectamine™ LTX and PLUS™ reagent (Invitrogen), vectors produced in the Example <2-3> were respectively transfected in Chinese hamster ovary cells which are a host cell producing a recombinant erythropoietin. The transfected Chinese hamster ovary cells were cultured in a media (an MEM-α media including 400 μg/ml Hygromycin B, 10% dFBS, 1% Antibiotics-antimycotics, 20 nM MTX), was incubated in a incubator with a condition of 5% $CO_2$ and 37° C. and selection and subculturing of survived cells were repeated.

<3-2> Identification of GNE/MNK Gene Expression

So as to identify expression of GNE/MNK gene which is introduced into selected cells in the Example <3-1>, the whole RNA was isolated by using TRIzol reagent (Invitrogen) from cultured cells. Gene expression was identified through RT-PCR. For RT-PCR, a forward primer (5'-GAC-CACCGACATTAAGCATTC-3': SEQ ID NO: 18) and a reverse primer (5'-GCGTCACAAAGTTCTCCTGTC-3': SEQ ID NO: 19), which were intended for identification of mutation-induced GNE/MNK expression, were used.

Figure 6:
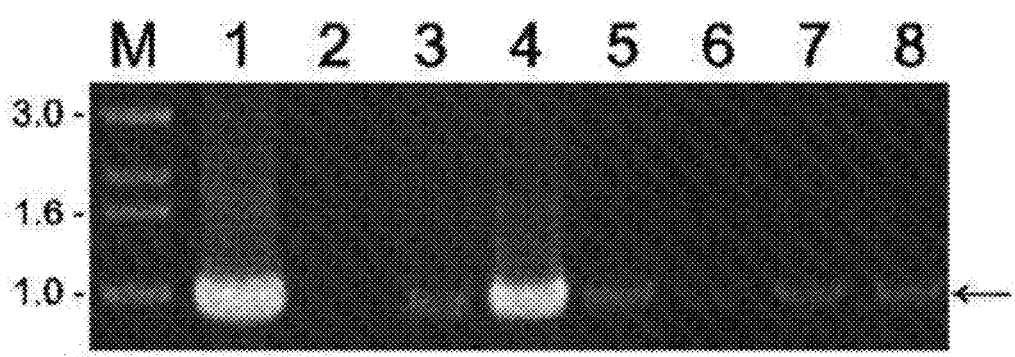
FIG. 6 is a diagram illustrating expression of point mutated GNE/MNK genes transfected in Chinese hamster ovary cells by RT-PCR.

As a result, as shown in FIG. 6, a significant high expression of point mutated GNE/MNK genes (EC2-1H9-rEK-R263L, EC2-1H9-rEk-R263L II-7, EC2-1H9-rEK-R263L II-12, EC2-1H9-rEK-R263L-R266Q 4, EC2-1H9-rEK-R263L-R266Q 7 and EC2-1H9-rEK-R263L-R266Q II-1) was identified in Chinese hamster ovary cells where pREP4-rEK-R263L and pREP4-rEK-R263L-R266Q were transfected (FIG. 6).

<3-3> Preparation and Purification of a Recombinant Erythropoietin

The cells were cultured for three days after it is injected into a T-175 flask, and is incubated for 48 hours after substitution by serum free media (CHO-S-SFM II, Sigma) to obtain a culture media. The obtained media was concentrated through ultrafiltration and a recombinant erythropoietin was purified through immune-affinity chromatography.

<3-4> Quantification of Intracellular CMP-Sialic Acid

After a predetermined number of cells were lysed to extract intracellular CMP-sialic acid using a sonic cell disruptor, HPLC analysis was performed by using CarboPac PA-1 and PA-1 guard column (Dionex, Sunnyvale, Calif.). So as to be compared to an addition method for N-acetyl mannosamine, 5.0 mM of ManNAc was added to SFM in the same condition with a wild type cell line and it was incubated for 48 hours. A concentration of intracellular CMP-sialic acid was measured and compared.

Figure 7:
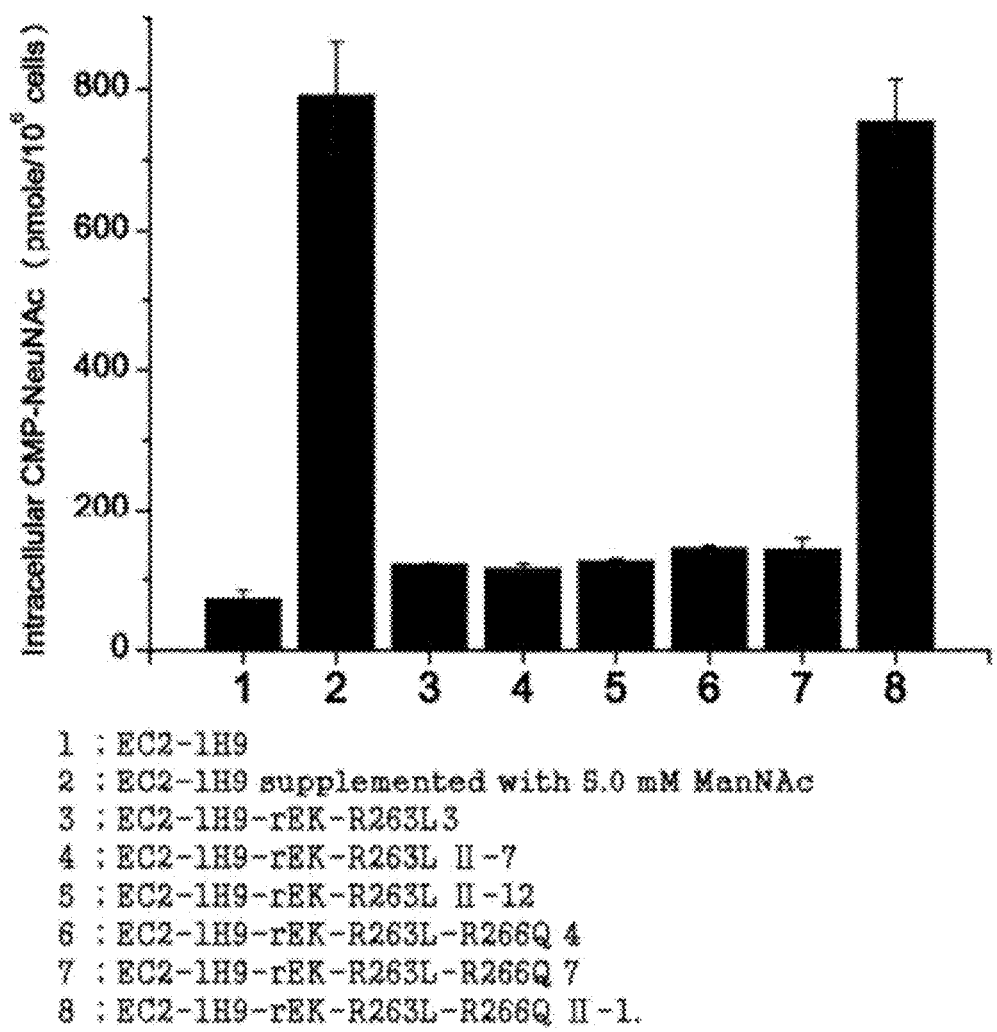
FIG. 7 is a graph illustrating intracellular CMP-sialic acid content by overexpression of point mutated GNE/MNK genes.

As a result, as shown in FIG. 7, intracellular CMP-sialic acid content was shown to increase in cells where pREP4-rEK-R263L or pREP4-rEK-R263L-R266Q were transfected compared to wild type Chinese hamster ovary cells. Particularly, for EC2-1H9-rEK-R263L-R266Q H-1, a significant increase in CMP-sialic acid content was identified compared to wild type cells.

EXAMPLE 4

Identification of a Change in Sialic Acid Content by Overexpression of Point Mutation-Induced GNE/MNK Genes, Human Alpha-2,3-Sialyltransferase Genes and CMP-Sialic Acid Transporter Genes <4-1> Introduction of Expression Vector of Point Mutation-Induced GNE/MNK, Human Alpha-2,3-Sialyltransferase and CMP-Sialic Acid Transporter Genes into Chinese Hamster Ovary Cells Three types of expression vector prepared in the <Example 2> is transfected in Chinese hamster ovary cells producing a recombinant erythropoietin or thrombopoietin by using Lipofectamine LTX™ and PLUS™ reagent (Invitrogen). The transfected Chinese hamster ovary cells producing a recombinant erythropoietin were cultured in MEM-α media including 500 μg/ml Zeoncin, 400 μg/ml Hygromycin B, 10% dFBS, 1% Antibiotics-Antimycotics, and 20 nM MTX, and the transfected Chinese hamster ovary cells producing a recombinant thrombopoietin were cultured in IMDM media including 300 μg/ml Zeoncin, 250 μg/ml Hygromycin B, 10% dFBS, 1% Antibiotics-Antimycotics, and 80 nM MTX, and then the cells were incubated in a incubator with a condition of 5% $CO_2$ and 37° C. and selection and subculturing of survived cells were repeated.

<4-2> Identification of Gene Expression

So as to identify expression of GNE/MNK genes, alpha-2,3-sialyltransferase genes, and a CMP-sialic acid transporter genes which were introduced into cell selected in the Example <4-1>, the whole RNA was isolated from the cultured cell by using TRIzol reagent (Invitrogen). Expression of point mutation-induced GNE/MNK genes, human alpha-2,3-sialyltransferase genes, and a CMP-sialic acid transporter genes was identified through RT-PCR by using a primer pair in Table 2 below. Furthermore, overexpression of CMP-sialic acid transporter genes from Chinese hamster ovary cells was identified by using real-time PCR.

TABLE 2

| | | |
|---|---|---|
| alpha-2,3-sialyl-transferase | forward primer reverse primer | 5'-GGAGGACTCCAATTCAGTGG-3' (SEQ ID NO: 20) 5'-TAGCCAAATCCTGCGACTGCC-3' (SEQ ID NO: 21) |
| GNE/MNK enzyme | forward primer reverse primer | 5'-GTGACCACCGACATTAAGCATTCC-3' (SEQ ID NO: 22) 5'-GAGCGTCACAAAGTTCTCCTGTCC-3' (SEQ ID NO: 23) |
| CMP-sialic acid transporter | forward primer reverse primer | 5'-GATAAGTGTTGGACTTTTA-3' (SEQ ID NO: 24) 5'-TCAGTTGATAGGTAACCT-3' (SEQ ID NO: 25) |

Figure 9:
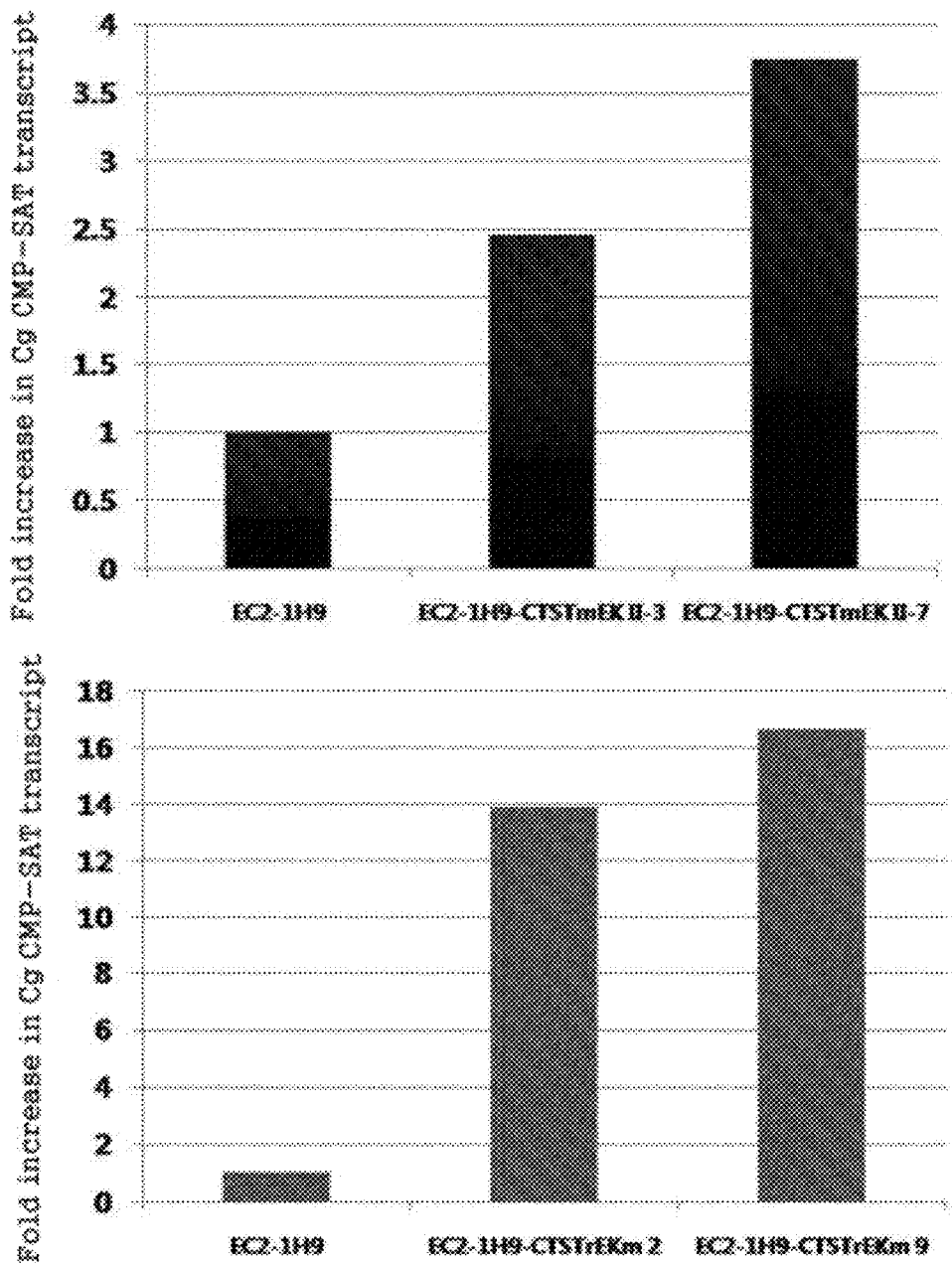
FIG. 9 is a graph illustrating the fold increase of CMP-sialic acid transporter transcripts in Chinese hamster ovary cells where point mutated GNE/MNK, human alpha-2,3-sialyltransferase and CMP-sialic acid transporter genes are transfected.

As a result, as shown in FIG. 8, in a host cell producing erythropoietin where point mutation-induced GNE/MNK, human alpha-2,3-sialyltransferase genes and CMP-sialic acid transporter genes are transfected, overexpression of alpha-2,3-sialyltransferase (A) genes and point mutation-induced GNE/MNK (B) genes was identified (FIG. 8). As shown in FIG. 9, overexpression amount of a CMP-sialic acid transporter transcript was shown to be significantly higher in a host cell producing erythropoietin where point mutation-induced GNE/MNK genes, human alpha-2,3-sialyltransferase genes and a CMP-sialic acid transporter are transfected than in wild type host cell (FIG. 9). Furthermore, in a host cell producing thrombopoietin where point mutation-induced GNE/MNK (pREP4-rEK-R263L-R266Q), human alpha-2,3-sialyltransferase genes and CMP-sialic acid transporter genes are transfected, overexpression of alpha-2,3-sialyltransferase genes, point mutation-induced GNE/MNK genes, CMP-sialic acid transporter genes were identified.

Accordingly, overexpression of the three types of genes was found to be induced in a host cell where erythropoietin or thrombopoietin is produced by transfection.

<4-3> Preparation and Purification of a Recombinant Glycoprotein

The transfected Chinese hamster ovary cells producing a recombinant erythropoietin or thrombopoietin were injected into a T-175 flask and cultured for three days. A culture media was obtained after its media was changed with SFM and incubated for 48 hours. The obtained media was concentrated through ultrafiltration and recombinant erythropoietin and recombinant thrombopoietin were purified by using immunoaffinity chromatography.

<4-4> Quantification of Intracellular CMP-Sialic Acid

Intracellular CMP-sialic acid was extracted by lysing a predetermined number of the cells and HPLC analysis was performed by using CarboPac PA-1 and PA-1 guard column (Dionex, Sunnyvale, Calif.). A mean value and a standard deviation were calculated through two independent experiments.

Figure 10:
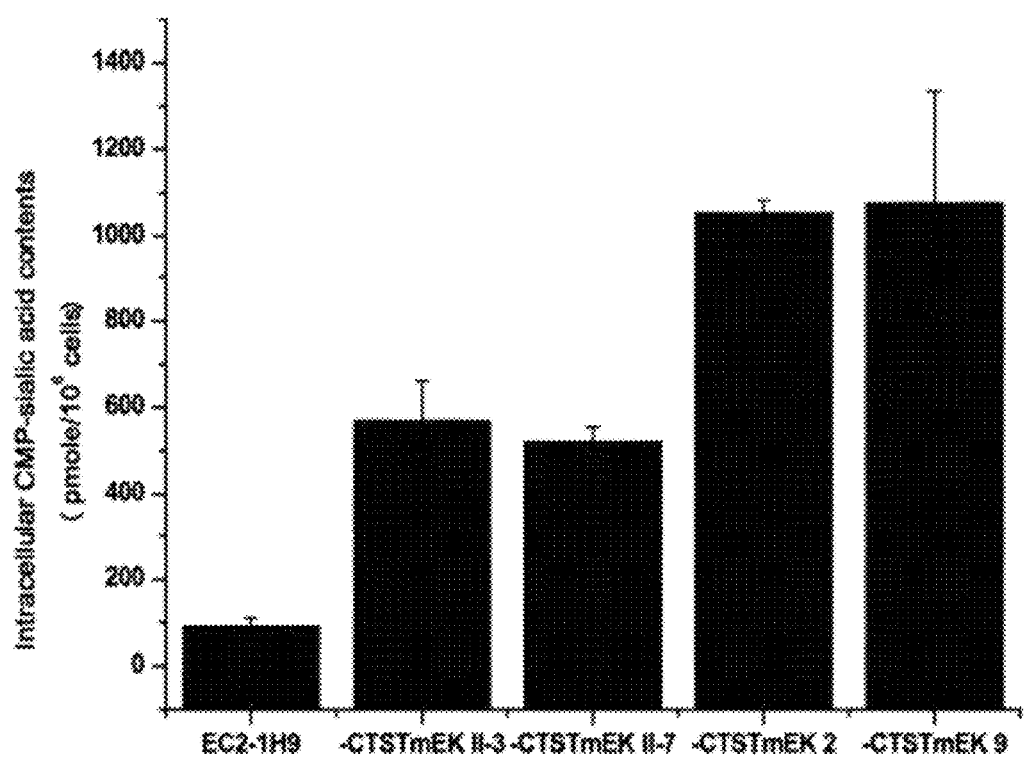
FIG. 10 is a graph illustrating intracellular CMP-sialic acid content in Chinese hamster ovary cells where point mutated GNE/MNK, human alpha-2,3-sialyltransferase and CMP-sialic acid transporter genes are transfected.

As a result, as shown in FIG. 10, intracellular CMP-sialic acid content was shown to be significantly higher in a host cell producing erythropoietin where point mutation-induced GNE/MNK, human alpha-2,3-sialyltransferase and CMP-sialic acid transporter genes are all transfected than in a wild type host cell (FIG. 10). Furthermore, intracellular CMP-sialic acid content was shown to be 10~12 times higher in a host cell producing thrombopoietin where point mutation-induced GNE/MNK, human alpha-2,3-sialyltransferase and CMP-sialic acid transporter genes are all transfected than in a wild type host cell.

<4-5> Identification of Erythropoietin Isoform

So as to isolate and compare isoform according to the total amount of molecular charge of erythropoietin, isoelectric focusing (IEF) analysis was performed. On the basis that sialic acid of erythropoietin glycan structure is negative charged, a change in sialic acid content in erythropoietin was identified. 10 μg of purified erythropoietin in pI 3~7 range was isolated through Novex precast IEF gel (pI 3~7, Invitrogen) according to manufacturer's instruction. The isolated isoform was visualized by Coomassie blue staining, and a intensity ratio of isoform band shown in pI 4.5 or less, for quantitative comparison, was analyzed through Multi gauge version 3.0 software.

Figure 11:
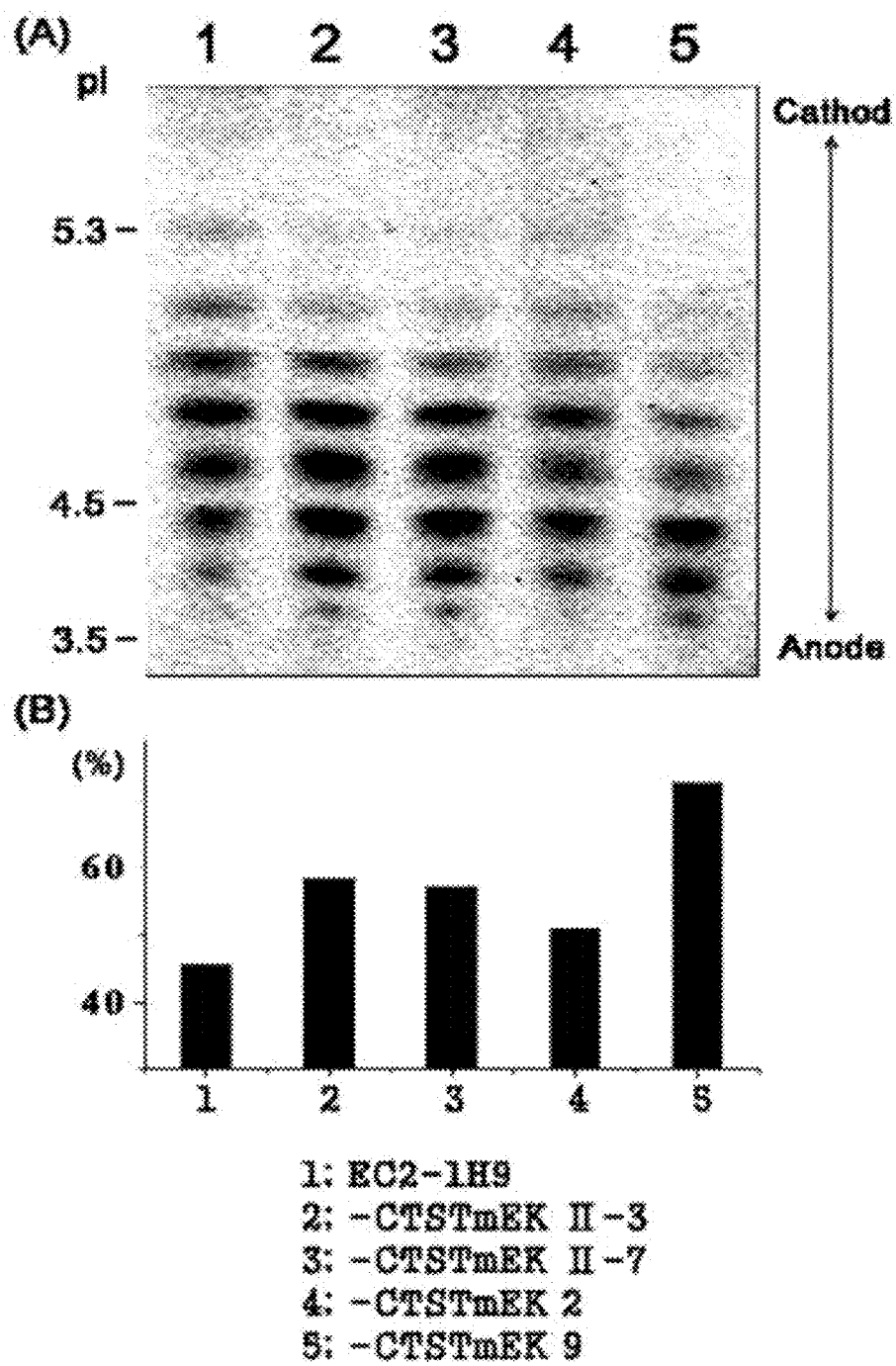
FIG. 11 is a diagram illustrating isoform of erythropoietin which moved to a negative charge, by isoelectric focusing (IEF) in Chinese hamster ovary cells where point mutated GNE/MNK, human alpha-2,3-sialyltransferase and CMP-sialic acid transporter genes are transfected.

As a result, as shown in FIG. 11, the whole isoforms was identified to move to negative charge in a host cell where point mutation-induced GNE/MNK, human alpha-2,3-sialyltransferase and CMP-sialic acid transporter genes were introduced, due to an increase in sialic acid. Particularly, EC2-1H9-CTSTrEKm cell line was shown to move the most clearly (FIG. 11).

<4-6> Analysis of Sialic Acid Content in a Recombinant Glycoprotein

Sialic acid of the purified recombinant erythropoietin or recombinant thrombopoietin was all isolated through mild hydrolysis and was tagged by o-phenylenediamine-2HCl (OPD). The tagged sialic acid was quantified through HPLC analysis by using C18-reversed-phase column. A mean value and a standard deviation were calculated through two independent experiments.

Figure 12:
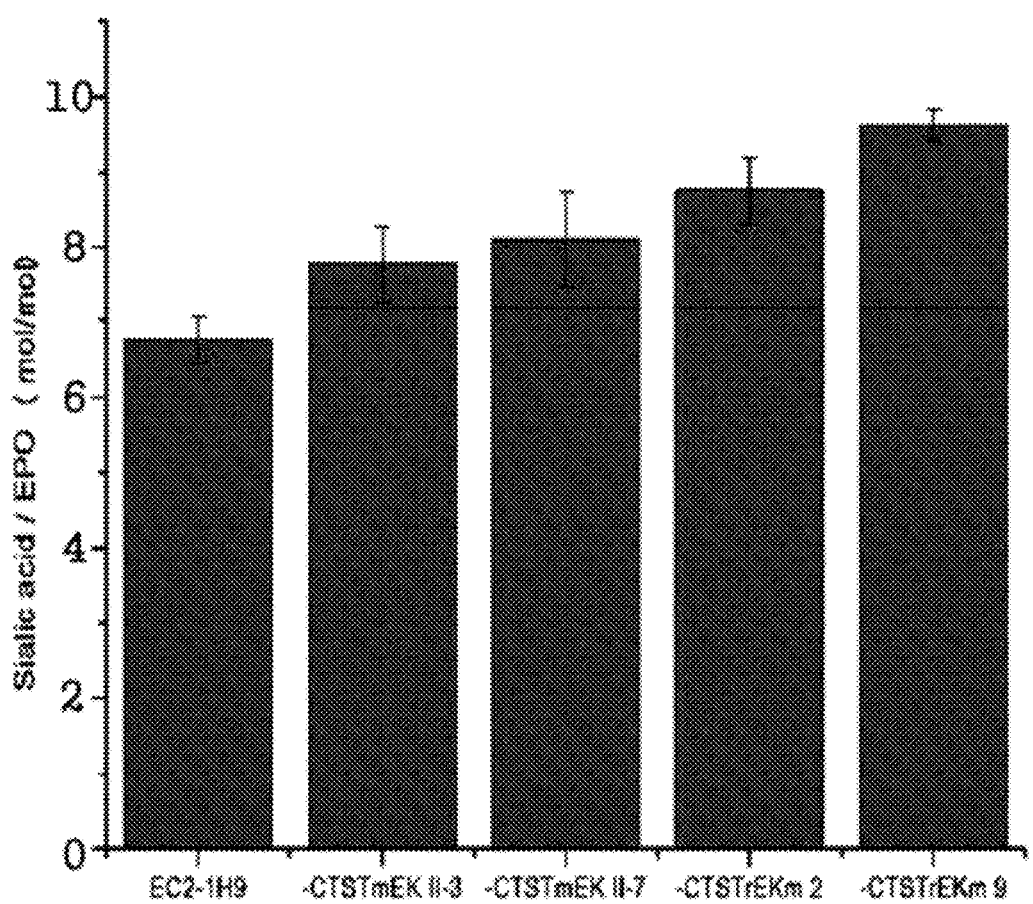
FIG. 12 is a graph illustrating sialic acid content of an recombinant erythropoietin in Chinese hamster ovary cells where point mutated GNE/MNK, human alpha-2,3-sialyltransferase and CMP-sialic acid transporter genes are transfected.
Figure 13:
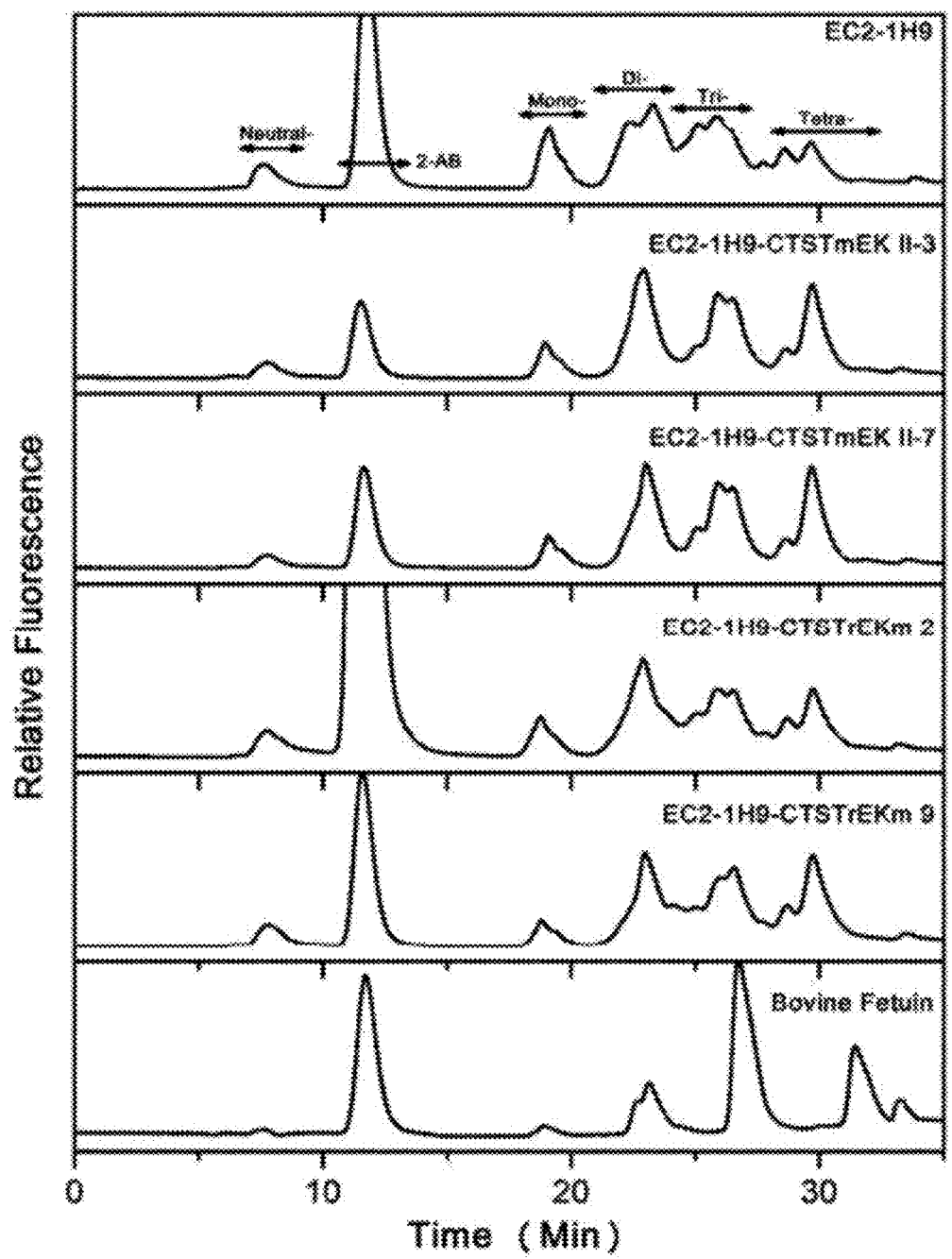
FIG. 13 is a diagram illustrating a sialylation profile of N-linked glycan of erythropoietin by anion exchange HPLC.

As a result, as shown in FIG. 12, erythropoietin-bound sialic acid content was shown to be significantly higher in a host cell where point mutation-induced GNE/MNK, human alpha-2,3-sialyltransferase and CMP-sialic acid transporter genes are all transfected than in a untransfected wild type host cell. For erythropoietin purified from EC2-1H9-CTSTrEKm 9 cell line, sialic acid content was identified as about 43% increase compared to a wild type (FIG. 12). Furthermore, thrombopoietin-bound sialic acid content was identified as about 20~30% increase in a host cell where point mutation-induced GNE/MNK, human alpha-2,3-sialyltransferase and CMP-sialic acid transporter genes are all transfected compared to thrombopoietin-bound sialic acid content in a untransfected wild type host cell.

Accordingly, sialic acid content of glycoprotein was identified to increase by overexpression of the three types of genes.

EXAMPLE 5

Identification of Sialylation Profile for Erythropoietin

So as to more precisely analyze a sialylation profile on N-linked glycan of erythropoietin, sialylation profile analysis was performed. So as to analyze based on the number of sialic acid contained in each N-linked glycan, 2-AB tagged N-linked glycan was analyzed by HPLC (Waters system) by using anion exchange column (TSKegel DEAE-5PW, 7.5 mm×75 mm; Tosh, Tokyo, Japan). Specifically, 20% aqueous acetonitrile (E1) and 250 mM ammonium formate and pH 9.0 acetonitrile (E2) were used for HPLC analysis. A Flow rate was 0.4 ml/min, column temperature was 30° C., It was analyzed by using 0% E2 for 5 minutes and then analyzed increasing the concentration up to 100% E2 for 35 minutes proportionately. It was analyzed by using fluorescence analyzer (Model 474; Waters) in 330 nm emission/420 nm excitation wavelength. Commercially available standard 2-AB-bovine fetuin N-linked glycan library (GLYKO; ProZyme) was analyzed together to determine the number of sialic acid with a peak respectively based on a retention time of a peak region of sialic acid number. A mean value and a standard deviation were calculated through two independent experiments.

As a result, as shown in Table 3 below and in FIG. 13, in all cell lines of the present invention, a ratio of neutral-sialylated glycan (asialo-) and mono-sialylated glycan which are free of sialic acid largely decreased, and a ratio of tetra-sialylated glycan was shown to largely increase up to 32%.

TABLE 3

A relative amount of sialylated N-linked glycans in erythropoietin analyzed by anion exchange HPLC

| sialylated glycans | Relative amounts of sialylated glycans (%) | | | | |
|---|---|---|---|---|---|
| | EC2-1H9 | -CTSTmEK II-3 | CTSTmEK II-7 | CTSTrEkm 2 | CTSTrEKm 9 |
| Neutral (asialo-) | 12.25 ± 4.19 | 4.63 ± 0.81 | 5.83 ± 3.43 | 7.63 ± 2.52 | 6.71 ± 1.92 |
| Mono- | 20.50 ± 0.11 | 9.02 ± 0.21 | 7.98 ± 0.50 | 13.74 ± 0.01 | 9.01 ± 0.66 |
| Di- | 30.03 ± 4.49 | 33.03 ± 0.02 | 29.70 ± 1.05 | 32.82 ± 1.16 | 27.73 ± 0.22 |
| Tri- | 23.27 ± 0.64 | 27.55 ± 1.53 | 28.33 ± 2.38 | 23.87 ± 2.41 | 24.53 ± 2.84 |
| Tetra- | 13.97 ± 0.83 | 25.79 ± 0.94 | 28.17 ± 0.49 | 21.95 ± 1.27 | 32.03 ± 0.48 |

INDUSTRIAL APPLICABILITY

As above, a recombinant glycoprotein with increased sialic acid content may be used in a useful way to develop and prepare a glycoprotein with excellent quality and bioequivalence by preventing internal degradation, by preparing the recombinant glycoprotein with increased sialic acid content which plays a key role in internal half life of a sialylated glycoprotein.

What is claimed is:

1. A method for preparing a glycoprotein with increased content of sialic acid, comprising:
   1) preparing an expression vector comprising a gene encoding UDP-GlcNAc 2-epimerase/ManNAc kinase (GNE/MNK) having an amino acid sequence with an arginine at position 263 substituted by leucine and an arginine at position 266 substituted by glutamine in an amino acid sequence represented by SEQ ID NO: 1, a gene encoding alpha-2,3-sialyltransferase having an amino acid sequence represented by SEQ ID NO: 4, and a gene encoding cytidine monophosphate (CMP)-sialic acid transporter having an amino acid sequence represented by SEQ ID NO: 5;
   2) transfecting the expression vector in Step 1) in a mammalian cell producing a sialylated glycoprotein to prepare a transfectant; and
   3) incubating the transfectant in Step 2) to purify a recombinant glycoprotein from the transfectant.

2. The method as set forth in claim 1, wherein the glycoprotein is one selected from the group consisting of erythropoietin, thrombopoietin, alpha-antitrypsin, cholinesterase, chorionic gonadotropin, CTLA4Ig, Factor VIII, gamma-glutamyltransferase, granulocyte colony-stimulating Factor (G-CSF) and luteinizing hormone (LH).

3. The method as set forth in claim 1, wherein the mammalian cell is one selected from the group consisting of Chinese hamster ovary cells (CHO), HT-1080, human lymphoblastoid, SP2/0 (mouse myeloma), NS0 (mouse myeloma), baby hamster kidney (BHK), human embryonic kidney cells (HEK) and PERC.6 (human retinal cells).

4. A method for preparing a cell with increased intracellular content of CMP-sialic acid, comprising:
   1) preparing an expression vector comprising a gene encoding UDP-GlcNAc 2-epimerase/ManNAc kinase (GNE/MNK) having an amino acid sequence with an arginine at position 263 substituted by leucine and an arginine at position 266 substituted by glutamine in an amino acid sequence represented by SEQ ID No: 1, a gene encoding alpha-2,3-sialyltransferase having an amino acid sequence represented by SEQ ID No: 4, and a gene encoding a CMP-sialic acid transporter having an amino acid sequence represented by SEQ ID No: 5; and
   2) transfecting the expression vector in Step 1) in a mammalian cell to prepare a transfectant.

* * * * *